United States Patent
Anderson et al.

(10) Patent No.: US 10,039,578 B2
(45) Date of Patent: *Aug. 7, 2018

(54) METHODS AND DEVICES FOR MINIMALLY INVASIVE SPINAL FIXATION ELEMENT PLACEMENT

(71) Applicant: DePuy Synthes Products, Inc., Raynham, MA (US)

(72) Inventors: David Greg Anderson, Moorestown, NJ (US); Christopher W. Sicvol, Boston, MA (US); George Joseph Ross, Rehoboth, MA (US); Sean P. Selover, Westport, MA (US); Ramon Alberto Ruberte, Durham, NC (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/230,385

(22) Filed: Aug. 6, 2016

(65) Prior Publication Data
US 2016/0338745 A1 Nov. 24, 2016

Related U.S. Application Data

(60) Continuation of application No. 14/853,093, filed on Sep. 14, 2015, now Pat. No. 9,750,547, which is a
(Continued)

(51) Int. Cl.
*A61B 17/88* (2006.01)
*A61F 5/00* (2006.01)
(Continued)

(52) U.S. Cl.
CPC .... *A61B 17/7085* (2013.01); *A61B 17/00234* (2013.01); *A61B 17/7011* (2013.01);
(Continued)

(58) Field of Classification Search
CPC ............ A61B 17/7032; A61B 17/7037; A61B 17/1671; A61B 17/1757;
(Continued)

(56) References Cited

U.S. PATENT DOCUMENTS

| 854,956 A | 5/1907 | Maritn |
| 1,472,464 A | 10/1923 | Ellison |

(Continued)

FOREIGN PATENT DOCUMENTS

| CA | 2 244 217 A1 | 8/1997 |
| CA | 2 577 436 A1 | 6/2006 |

(Continued)

OTHER PUBLICATIONS

[No Author Listed] DePuy AcroMed Product Brochure "micro'TLIF, A Mini-Open and Intermuscular Transforaminal Lumbar Interbody Fusion" Aperture Spinal System, (22 pages) Oct. 2002.
(Continued)

*Primary Examiner* — Ann Schillinger
(74) *Attorney, Agent, or Firm* — Nutter McClennen & Fish LLP

(57) ABSTRACT

Minimally invasive methods and devices for introducing a spinal fixation element into a surgical site in a patient's spinal column are provided. In general, the method involves advancing a spinal fixation element in a first, lengthwise orientation along a pathway extending from a minimally invasive percutaneous incision to a spinal anchor site. As the spinal fixation element approaches the spinal anchor site, the fixation element can be manipulated to extend in a second orientation, which is preferably substantially transverse to the first orientation, to position the fixation element in relation to one or more spinal anchors.

22 Claims, 23 Drawing Sheets

Related U.S. Application Data continuation of application No. 14/251,467, filed on Apr. 11, 2014, now Pat. No. 9,161,786, which is a continuation of application No. 13/309,944, filed on Dec. 2, 2011, now Pat. No. 8,734,490, which is a continuation of application No. 12/365,711, filed on Feb. 4, 2009, now Pat. No. 8,105,361, which is a division of application No. 10/738,130, filed on Dec. 16, 2003, now Pat. No. 7,527,638.

(51) Int. Cl.
  *A61B 17/70* (2006.01)
  *A61B 17/00* (2006.01)

(52) U.S. Cl.
  CPC ...... *A61B 17/7037* (2013.01); *A61B 17/7074* (2013.01); *A61B 17/7035* (2013.01); *Y10S 606/914* (2013.01)

(58) Field of Classification Search
  CPC ........ A61B 2017/0256; A61B 17/7035; A61B 17/3421; A61B 17/70
  See application file for complete search history.

(56) References Cited

U.S. PATENT DOCUMENTS

| | | |
|---|---|---|
| 2,243,717 A | 5/1941 | Moreira |
| 2,320,709 A | 6/1943 | Amesen |
| 2,346,346 A | 4/1944 | Anderson |
| 2,362,999 A | 11/1944 | Hewitt |
| 2,524,095 A | 10/1950 | Williams et al. |
| 2,531,892 A | 11/1950 | Reese |
| 2,532,972 A | 12/1950 | Vertin |
| 2,548,729 A | 4/1951 | Kumpman |
| 2,579,438 A | 12/1951 | Longfellow |
| 2,669,896 A | 2/1954 | Clough |
| 2,813,450 A | 11/1957 | Dzus |
| 3,013,244 A | 12/1961 | Rudy |
| 3,236,275 A | 2/1966 | Smith |
| 3,246,646 A | 4/1966 | Murphy |
| 3,552,799 A | 1/1971 | Koranda |
| 3,604,487 A | 9/1971 | Gilbert |
| 3,640,416 A | 2/1972 | Temple |
| 3,997,138 A | 12/1976 | Crock et al. |
| 4,033,139 A | 7/1977 | Frederick |
| 4,041,939 A | 8/1977 | Hall |
| 4,190,091 A | 2/1980 | Colognori |
| 4,263,899 A | 4/1981 | Burgin |
| 4,269,178 A | 5/1981 | Keene |
| 4,347,845 A | 9/1982 | Mayfield |
| 4,373,754 A | 2/1983 | Bollfrass et al. |
| 4,409,968 A | 10/1983 | Drummond |
| 4,448,191 A | 5/1984 | Rodnyansky et al. |
| 4,461,281 A | 7/1984 | Carson |
| 4,484,570 A | 11/1984 | Sutter et al. |
| 4,537,448 A | 8/1985 | Ketterer |
| 4,545,374 A | 10/1985 | Jacobson |
| 4,573,448 A | 3/1986 | Kambin |
| 4,600,224 A | 7/1986 | Blose |
| 4,653,486 A | 3/1987 | Coker |
| 4,686,966 A | 8/1987 | Tsai |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,765,311 A | 8/1988 | Kulik et al. |
| 4,790,297 A | 12/1988 | Luque |
| 4,836,196 A | 6/1989 | Park et al. |
| 4,838,264 A | 6/1989 | Bremer et al. |
| 4,872,451 A | 10/1989 | Moore et al. |
| 4,877,020 A | 10/1989 | Vich et al. |
| 4,887,020 A | 12/1989 | Graham |
| 4,887,596 A | 12/1989 | Sherman |
| 4,913,134 A | 4/1990 | Luque |
| 4,946,458 A | 8/1990 | Harms et al. |
| 4,950,269 A | 8/1990 | Gaines, Jr. |
| 4,961,740 A | 10/1990 | Ray et al. |
| 5,005,562 A | 4/1991 | Cotrel |
| 5,015,247 A | 5/1991 | Michelson |
| 5,015,255 A | 5/1991 | Kuslich |
| 5,019,080 A | 5/1991 | Hemer |
| 5,020,519 A | 6/1991 | Hayes et al. |
| 5,022,791 A | 6/1991 | Isler |
| 5,024,659 A | 6/1991 | Sjostrom |
| 5,034,011 A | 7/1991 | Howland |
| 5,052,372 A | 10/1991 | Shapiro |
| 5,067,955 A | 11/1991 | Cotrel |
| 5,084,048 A | 1/1992 | Jacob |
| 5,084,053 A | 1/1992 | Ender |
| 5,092,635 A | 3/1992 | DeLange et al. |
| 5,092,866 A | 3/1992 | Breard et al. |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,171,279 A | 12/1992 | Mathews |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,231,973 A | 8/1993 | Dickie |
| 5,242,443 A | 9/1993 | Kambin |
| 5,242,446 A | 9/1993 | Steffee et al. |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,862 A | 2/1994 | Baker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,324,290 A | 6/1994 | Zdeblick et al. |
| 5,330,472 A | 7/1994 | Metz-Stavenhagen |
| 5,334,203 A | 8/1994 | Wagner |
| 5,346,493 A | 9/1994 | Stahurski et al. |
| 5,354,292 A | 10/1994 | Braeuer et al. |
| 5,357,983 A | 10/1994 | Mathews |
| 5,358,289 A | 10/1994 | Banker et al. |
| 5,360,431 A | 11/1994 | Puno et al. |
| 5,367,983 A | 11/1994 | Pound et al. |
| 5,375,823 A | 12/1994 | Navas et al. |
| 5,385,583 A | 1/1995 | Cotrel |
| 5,395,317 A | 3/1995 | Kambin |
| 5,395,371 A | 3/1995 | Miller et al. |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,439,464 A | 8/1995 | Shapiro |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,520,610 A | 5/1996 | Giglio et al. |
| 5,534,001 A | 7/1996 | Schlapfer et al. |

(56) References Cited

U.S. PATENT DOCUMENTS

| | | |
|---|---|---|
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,248 A | 10/1996 | Mathews |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,391 A | 11/1997 | Boyd |
| 5,683,392 A | 11/1997 | Richelsoph et al. |
| 5,690,630 A | 11/1997 | Enrico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico |
| 5,728,097 A | 3/1998 | Mathews |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,741,261 A | 4/1998 | Moskowitz et al. |
| 5,749,884 A | 5/1998 | Benderev et al. |
| 5,752,957 A | 5/1998 | Ralph et al. |
| 5,762,629 A | 6/1998 | Kambin |
| 5,766,221 A | 6/1998 | Benderev et al. |
| 5,782,830 A | 7/1998 | Farris |
| 5,782,833 A | 7/1998 | Haider |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,817,094 A | 10/1998 | Errico et al. |
| 5,855,151 A | 1/1999 | Habermehl |
| 5,863,293 A | 1/1999 | Richelsoph |
| 5,865,487 A | 2/1999 | Gore et al. |
| 5,873,878 A | 2/1999 | Harms et al. |
| 5,876,402 A | 3/1999 | Enrico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,891,147 A | 4/1999 | Moskowitz et al. |
| 5,897,590 A | 4/1999 | Donovan |
| 5,902,231 A | 5/1999 | Foley et al. |
| RE36,221 E | 6/1999 | Breard et al. |
| 5,910,141 A | 6/1999 | Morrison et al. |
| 5,928,139 A | 7/1999 | Koros et al. |
| 5,931,777 A | 8/1999 | Sava |
| 5,938,663 A | 8/1999 | Petreto |
| 5,944,465 A | 8/1999 | Janitzki |
| 5,951,553 A | 9/1999 | Betz et al. |
| 5,954,635 A | 9/1999 | Foley et al. |
| 5,954,725 A | 9/1999 | Sherman et al. |
| 5,961,517 A | 10/1999 | Biedermann et al. |
| 5,964,760 A | 10/1999 | Richelsoph |
| 5,984,923 A | 11/1999 | Breard |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,033,406 A | 3/2000 | Mathews |
| 6,053,917 A | 4/2000 | Sherman et al. |
| 6,059,786 A | 5/2000 | Jackson |
| 6,063,088 A | 5/2000 | Winslow |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat et al. |
| 6,102,912 A | 8/2000 | Cazin et al. |
| 6,102,913 A | 8/2000 | Jackson |
| 6,106,526 A | 8/2000 | Harms et al. |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,493 A | 10/2000 | Koros et al. |
| 6,139,549 A | 10/2000 | Keller |
| 6,143,032 A | 11/2000 | Schafer et al. |
| 6,146,383 A | 11/2000 | Studer et al. |
| 6,159,179 A | 12/2000 | Simonson |
| 6,183,472 B1 | 2/2001 | Lutz |
| 6,186,718 B1 | 2/2001 | Fogard |
| 6,187,005 B1 | 2/2001 | Brace et al. |
| 6,189,422 B1 | 2/2001 | Stihl |
| 6,193,720 B1 | 2/2001 | Yuan et al. |
| 6,200,322 B1 | 3/2001 | Branch et al. |
| 6,214,012 B1 | 4/2001 | Karpman et al. |
| RE37,161 E | 5/2001 | Michelson et al. |
| 6,224,545 B1 | 5/2001 | Cocchia et al. |
| 6,224,596 B1 | 5/2001 | Jackson |
| 6,224,598 B1 | 5/2001 | Jackson |
| 6,226,548 B1 | 5/2001 | Foley et al. |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,888 B1 | 10/2001 | Mellinger et al. |
| 6,309,391 B1 | 10/2001 | Crandall et al. |
| 6,315,564 B1 | 11/2001 | Levisman |

(56) References Cited

U.S. PATENT DOCUMENTS

| | | |
|---|---|---|
| 6,315,779 B1 | 11/2001 | Morrison et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,371,968 B1 | 4/2002 | Kogasaka et al. |
| 6,379,356 B1 | 4/2002 | Jackson |
| 6,402,752 B2 | 6/2002 | Schaffler-Wachter et al. |
| 6,402,757 B1 | 6/2002 | Moore, III et al. |
| 6,440,133 B1 | 8/2002 | Beale et al. |
| 6,440,137 B1 | 8/2002 | Horvath et al. |
| 6,443,956 B1 | 9/2002 | Ray |
| 6,451,021 B1 | 9/2002 | Ralph et al. |
| 6,471,703 B1 | 10/2002 | Ashman |
| 6,471,705 B1 | 10/2002 | Biedermann et al. |
| 6,478,795 B1 | 11/2002 | Gournay et al. |
| 6,478,798 B1 | 11/2002 | Howland |
| 6,478,800 B1 | 11/2002 | Fraser et al. |
| 6,478,801 B1 | 11/2002 | Ralph et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,511,484 B2 | 1/2003 | Torode et al. |
| 6,520,907 B1 | 2/2003 | Foley et al. |
| 6,520,962 B1 | 2/2003 | Taylor et al. |
| 6,527,804 B1 | 3/2003 | Gauchet et al. |
| 6,530,926 B1 | 3/2003 | Davison |
| 6,530,929 B1 | 3/2003 | Justis et al. |
| 6,533,786 B1 | 3/2003 | Needham et al. |
| 6,539,826 B2 | 4/2003 | Oesterle et al. |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,038 B1 | 5/2003 | Morrison |
| 6,562,040 B1 | 5/2003 | Wagner |
| 6,565,565 B1 | 5/2003 | Yuan et al. |
| 6,565,567 B1 | 5/2003 | Haider |
| 6,572,618 B1 | 6/2003 | Morrison |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,599,294 B2 | 7/2003 | Fuss et al. |
| 6,648,887 B2 | 7/2003 | Ashman |
| 6,602,255 B1 | 8/2003 | Campbell et al. |
| 6,607,530 B1 | 8/2003 | Carl et al. |
| 6,610,063 B2 | 8/2003 | Kumar et al. |
| 6,613,050 B1 | 9/2003 | Wagner et al. |
| 6,616,667 B1 | 9/2003 | Steiger et al. |
| 6,616,669 B2 | 9/2003 | Ogilvie et al. |
| 6,623,484 B2 | 9/2003 | Betz et al. |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,059 B2 | 10/2003 | Randall et al. |
| 6,635,060 B2 | 10/2003 | Hanson et al. |
| 6,648,885 B1 | 11/2003 | Friesem |
| 6,648,888 B1 | 11/2003 | Shluzas |
| 6,652,526 B1 | 11/2003 | Arafiles |
| 6,652,527 B2 | 11/2003 | Zucherman et al. |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,660,006 B2 | 12/2003 | Markworth et al. |
| 6,663,632 B1 | 12/2003 | Frigg |
| 6,663,635 B2 | 12/2003 | Frigg et al. |
| 6,666,891 B2 | 12/2003 | Boehm, Jr. et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,248 B2 | 3/2004 | Jackson |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,687 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,740,089 B2 | 5/2004 | Haider |
| 6,743,231 B1 | 6/2004 | Gray et al. |
| 6,746,449 B2 | 6/2004 | Jones et al. |
| 6,746,454 B2 | 6/2004 | Winterbottom et al. |
| 6,749,614 B2 | 6/2004 | Teitelbaum et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,719 B2 | 7/2004 | Justis et al. |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,793,656 B1 | 9/2004 | Mathews |
| 6,802,844 B2 | 10/2004 | Ferree |
| 6,821,277 B2 | 11/2004 | Teitelbaum |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,835,205 B2 | 12/2004 | Atkinson et al. |
| 6,837,889 B2 | 1/2005 | Shluzas |
| 6,840,940 B2 | 1/2005 | Ralph et al. |
| 6,843,791 B2 | 1/2005 | Serhan |
| 6,849,064 B2 | 2/2005 | Hamada |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,899,713 B2 | 5/2005 | Shaolian et al. |
| 6,905,500 B2 | 6/2005 | Jeon et al. |
| 6,929,647 B2 | 8/2005 | Cohen |
| 6,932,817 B2 | 8/2005 | Baynham et al. |
| 6,932,820 B2 | 8/2005 | Osman |
| 6,932,822 B2 | 8/2005 | Oribe et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |

(56) References Cited

U.S. PATENT DOCUMENTS

| | | |
|---|---|---|
| 6,986,771 B2 | 1/2006 | Paul et al. |
| 6,989,011 B2 | 1/2006 | Paul et al. |
| 6,991,632 B2 | 1/2006 | Ritland |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,160,300 B2 | 1/2007 | Jackson |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,061 B2 | 2/2007 | Horton et al. |
| 7,179,225 B2 | 2/2007 | Shluzas et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,235,075 B1 | 6/2007 | Metz-Stavenhagen |
| 7,250,052 B2 | 7/2007 | Landry et al. |
| 7,264,621 B2 | 9/2007 | Coates et al. |
| 7,270,665 B2 | 9/2007 | Morrison et al. |
| 7,282,064 B2 | 10/2007 | Chin |
| 7,290,347 B2 | 11/2007 | Augostino et al. |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,377,922 B2 | 5/2008 | Barker |
| 7,445,627 B2 | 11/2008 | Hawkes et al. |
| 7,470,279 B2 | 12/2008 | Jackson |
| 7,476,228 B2 | 1/2009 | Abdou |
| 7,476,238 B2 | 1/2009 | Panjabi |
| 7,479,156 B2 | 1/2009 | Lourdel et al. |
| 7,491,208 B2 | 2/2009 | Pond, Jr. et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,638 B2 * | 5/2009 | Anderson ........ A61B 17/00234 606/279 |
| 7,527,640 B2 | 5/2009 | Ziolo et al. |
| 7,530,992 B2 | 5/2009 | Biedermann et al. |
| 7,547,318 B2 | 6/2009 | Birkmeyer et al. |
| 7,556,639 B2 | 7/2009 | Rothman et al. |
| 7,559,942 B2 | 7/2009 | Paul et al. |
| 7,559,943 B2 | 7/2009 | Mujwid |
| 7,563,264 B2 | 7/2009 | Landry et al. |
| 7,563,274 B2 | 7/2009 | Justis et al. |
| 7,563,275 B2 | 7/2009 | Falahee et al. |
| 7,563,283 B2 | 7/2009 | Kwak |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,589 B2 | 9/2009 | Falahee |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,601,171 B2 | 10/2009 | Ainsworth et al. |
| 7,604,653 B2 | 10/2009 | Kitchen |
| 7,604,654 B2 | 10/2009 | Fallin et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,618,440 B2 | 11/2009 | Gray et al. |
| 7,618,443 B2 | 11/2009 | Abdou |
| 7,618,444 B2 | 11/2009 | Shluzas |
| 7,621,912 B2 | 11/2009 | Harms et al. |
| 7,621,918 B2 | 11/2009 | Jackson |
| 7,621,940 B2 | 11/2009 | Harms et al. |
| 7,621,941 B2 | 11/2009 | Schlapfer et al. |
| 7,625,393 B2 | 12/2009 | Fallin et al. |
| 7,625,394 B2 | 12/2009 | Molz, IV et al. |
| 7,632,292 B2 | 12/2009 | Sengupta et al. |
| 7,632,293 B2 | 12/2009 | Hartmann |
| 7,641,670 B2 | 1/2010 | Davison et al. |
| 7,641,673 B2 | 1/2010 | Le Couedic et al. |
| 7,641,674 B2 | 1/2010 | Young |
| 7,645,294 B2 | 1/2010 | Kalfas et al. |
| 7,648,522 B2 | 1/2010 | David |
| 7,651,502 B2 | 1/2010 | Jackson |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,666,188 B2 | 2/2010 | Anderson et al. |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,375 B2 | 3/2010 | Ritland |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,475 B2 | 4/2010 | Justis et al. |
| 7,695,496 B2 | 4/2010 | Labrom et al. |
| 7,695,497 B2 | 4/2010 | Cordaro et al. |
| 7,695,498 B2 | 4/2010 | Ritland |
| 7,695,514 B2 | 4/2010 | Kwak |
| 7,699,872 B2 | 4/2010 | Farris et al. |
| 7,699,875 B2 | 4/2010 | Timm |

(56) References Cited

U.S. PATENT DOCUMENTS

| | | |
|---|---|---|
| 7,699,876 B2 | 4/2010 | Barry et al. |
| 7,704,271 B2 | 4/2010 | Abdou |
| 7,708,763 B2 | 5/2010 | Selover et al. |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,260 B2 | 6/2010 | Albert et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,736,305 B2 | 6/2010 | DiPoto |
| 7,749,258 B2 | 7/2010 | Biedermann et al. |
| 7,758,618 B2 | 7/2010 | Walder et al. |
| 7,763,048 B2 | 7/2010 | Fortin et al. |
| 7,763,052 B2 | 7/2010 | Jahng |
| 7,763,057 B2 | 7/2010 | Abdelgany et al. |
| 7,766,915 B2 | 8/2010 | Jackson |
| 7,766,941 B2 | 8/2010 | Paul |
| 7,766,942 B2 | 8/2010 | Patterson et al. |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,776,040 B2 | 8/2010 | Markworth et al. |
| 7,776,067 B2 | 8/2010 | Jackson |
| 7,776,071 B2 | 8/2010 | Fortin et al. |
| 7,776,075 B2 | 8/2010 | Bruneau et al. |
| 7,780,706 B2 | 8/2010 | Marino et al. |
| 7,785,349 B2 | 8/2010 | Walder et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,309 B2 | 10/2010 | Timm et al. |
| 7,811,310 B2 | 10/2010 | Baker et al. |
| 7,815,650 B2 | 10/2010 | Shluzas et al. |
| 7,815,663 B2 | 10/2010 | Trieu |
| 7,815,664 B2 | 10/2010 | Sherman et al. |
| 7,815,665 B2 | 10/2010 | Jahng et al. |
| 7,819,902 B2 | 10/2010 | Abdelgany et al. |
| 7,824,430 B2 | 11/2010 | Allard et al. |
| 7,833,250 B2 | 11/2010 | Jackson |
| 7,833,252 B2 | 11/2010 | Justis et al. |
| 7,854,751 B2 | 12/2010 | Sicvol et al. |
| 7,887,539 B2 | 2/2011 | Dunbar, Jr. et al. |
| 7,914,558 B2 | 3/2011 | Landry et al. |
| 7,955,355 B2 | 6/2011 | Chin |
| 7,985,242 B2 | 7/2011 | Forton et al. |
| 8,002,798 B2 | 8/2011 | Chin et al. |
| 8,034,084 B2 | 10/2011 | Landry et al. |
| 8,052,720 B2 | 11/2011 | Kuester et al. |
| 8,075,592 B2 | 12/2011 | Landry et al. |
| 8,100,915 B2 | 1/2012 | Jackson |
| 8,105,361 B2 | 1/2012 | Anderson et al. |
| 8,162,948 B2 | 4/2012 | Jackson |
| 8,277,491 B2 | 10/2012 | Selover et al. |
| 8,377,067 B2 | 2/2013 | Jackson |
| 8,500,780 B2 | 8/2013 | Petit et al. |
| 8,518,080 B2 | 8/2013 | Egli et al. |
| 8,734,490 B2 | 5/2014 | Anderson et al. |
| 9,101,415 B2 | 8/2015 | Jackson |
| 9,161,786 B2 * | 10/2015 | Anderson ........ A61B 17/00234 |
| 9,211,150 B2 | 12/2015 | Jackson |
| 9,750,547 B2 | 9/2017 | Anderson et al. |
| 2001/0001119 A1 | 5/2001 | Lombardo |
| 2001/0007941 A1 | 7/2001 | Steiner et al. |
| 2001/0010000 A1 | 7/2001 | Gertzbein et al. |
| 2001/0012937 A1 | 8/2001 | Schaffler-Wachter et al. |
| 2001/0023350 A1 | 9/2001 | Choi |
| 2001/0025553 A1 | 10/2001 | Oesterle et al. |
| 2001/0027318 A1 | 10/2001 | Oribe et al. |
| 2001/0029375 A1 | 10/2001 | Betz et al. |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donna et al. |
| 2001/0047175 A1 | 11/2001 | Doubler et al. |
| 2002/0004683 A1 | 1/2002 | Michelson |
| 2002/0007184 A1 | 1/2002 | Ogilvie et al. |
| 2002/0010467 A1 | 1/2002 | Cooper et al. |
| 2002/0011600 A1 | 1/2002 | Kurahashi et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0029040 A1 | 3/2002 | Morrison et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0045898 A1 | 4/2002 | Freid et al. |
| 2002/0045899 A1 | 4/2002 | Errico et al. |
| 2002/0045904 A1 | 4/2002 | Fuss et al. |
| 2002/0049368 A1 | 4/2002 | Ritland |
| 2002/0049446 A1 | 4/2002 | Harkey et al. |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0058950 A1 | 5/2002 | Winterbottom et al. |
| 2002/0068941 A1 | 6/2002 | Hanson et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082598 A1 | 6/2002 | Teitelbaum |
| 2002/0082600 A1 | 6/2002 | Shaolian et al. |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0091390 A1 | 7/2002 | Michelson |
| 2002/0095153 A1 | 7/2002 | Jones et al. |
| 2002/0103487 A1 | 8/2002 | Errico et al. |
| 2002/0111626 A1 | 8/2002 | Ralph et al. |
| 2002/0111628 A1 | 8/2002 | Ralph et al. |
| 2002/0116000 A1 | 8/2002 | Zucherman et al. |
| 2002/0116001 A1 | 8/2002 | Schafer et al. |
| 2002/0116006 A1 | 8/2002 | Cohen |
| 2002/0120270 A1 | 8/2002 | Trieu et al. |
| 2002/0123668 A1 | 9/2002 | Ritland |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0169448 A1 | 11/2002 | Vanacker |
| 2002/0173789 A1 | 11/2002 | Howland |
| 2002/0173791 A1 | 11/2002 | Howland |
| 2002/0193795 A1 | 12/2002 | Gertzbein et al. |
| 2002/0198526 A1 | 12/2002 | Shaolian et al. |
| 2003/0004519 A1 | 1/2003 | Torode et al. |
| 2003/0023240 A1 | 1/2003 | Amrein et al. |
| 2003/0023243 A1 | 1/2003 | Biedermann et al. |
| 2003/0055426 A1 | 3/2003 | Carbone et al. |
| 2003/0060826 A1 | 3/2003 | Foley et al. |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |

(56) References Cited

U.S. PATENT DOCUMENTS

| | | |
|---|---|---|
| 2003/0083667 A1 | 5/2003 | Ralph et al. |
| 2003/0083688 A1 | 5/2003 | Simonson |
| 2003/0083689 A1 | 5/2003 | Simonson |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0149432 A1 | 8/2003 | Frigg et al. |
| 2003/0150897 A1 | 8/2003 | Ng |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176862 A1 | 9/2003 | Taylor et al. |
| 2003/0176863 A1 | 9/2003 | Ueyama et al. |
| 2003/0181913 A1 | 9/2003 | Lieberman |
| 2003/0191371 A1 | 10/2003 | Smith et al. |
| 2003/0191469 A1 | 10/2003 | Ralph et al. |
| 2003/0191470 A1 | 10/2003 | Ritland |
| 2003/0195549 A1 | 10/2003 | Davison et al. |
| 2003/0195550 A1 | 10/2003 | Davison et al. |
| 2003/0195551 A1 | 10/2003 | Davison et al. |
| 2003/0199872 A1 | 10/2003 | Markworth et al. |
| 2003/0199873 A1 | 10/2003 | Richelsoph |
| 2003/0199874 A1 | 10/2003 | Michelson |
| 2003/0199885 A1 | 10/2003 | Davison et al. |
| 2003/0208203 A1 | 11/2003 | Lim et al. |
| 2003/0208204 A1 | 11/2003 | Bailey et al. |
| 2003/0208275 A1 | 11/2003 | Michelson |
| 2003/0212398 A1 | 11/2003 | Jackson |
| 2003/0216735 A1 | 11/2003 | Altarac et al. |
| 2003/0216748 A1 | 11/2003 | Gitis et al. |
| 2003/0216768 A1 | 11/2003 | Gitis et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0002708 A1 | 1/2004 | Ritland |
| 2004/0006301 A1 | 1/2004 | Sell et al. |
| 2004/0006342 A1 | 1/2004 | Altarac et al. |
| 2004/0006344 A1 | 1/2004 | Nguyen et al. |
| 2004/0034351 A1 | 2/2004 | Sherman et al. |
| 2004/0039383 A1 | 2/2004 | Jackson |
| 2004/0039384 A1 | 2/2004 | Boehm et al. |
| 2004/0039385 A1 | 2/2004 | Mazda et al. |
| 2004/0044335 A1 | 3/2004 | de la Torre et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0082961 A1 | 4/2004 | Teitelbaum |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0116929 A1 | 6/2004 | Barker et al. |
| 2004/0122442 A1 | 6/2004 | Lewis |
| 2004/0133207 A1 | 7/2004 | Abdou |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0147937 A1 | 7/2004 | Dunbar et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0172022 A1 | 9/2004 | Landry et al. |
| 2004/0172025 A1 | 9/2004 | Drewry et al. |
| 2004/0172031 A1 | 9/2004 | Rubecamp et al. |
| 2004/0176766 A1 | 9/2004 | Shluzas |
| 2004/0176776 A1 | 9/2004 | Zubok et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0186776 A1 | 9/2004 | Llach |
| 2004/0210216 A1 | 10/2004 | Farris et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249378 A1 | 12/2004 | Saint Martin et al. |
| 2004/0249380 A1 | 12/2004 | Glascott |
| 2004/0254574 A1 | 12/2004 | Morrison et al. |
| 2004/0260284 A1 | 12/2004 | Parker |
| 2004/0267260 A1 | 12/2004 | Mack et al. |
| 2004/0267264 A1 | 12/2004 | Konieczynski et al. |
| 2004/0267277 A1 | 12/2004 | Zannis et al. |
| 2005/0010219 A1 | 1/2005 | Dalton |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0038434 A1 | 2/2005 | Mathews |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0080418 A1 | 4/2005 | Simonson et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096653 A1 | 5/2005 | Doubler et al. |
| 2005/0096654 A1 | 5/2005 | Lin |
| 2005/0096748 A1 | 5/2005 | Yoon |
| 2005/0107788 A1 | 5/2005 | Beaurain et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0131421 A1 | 6/2005 | Anderson et al. |

(56) References Cited

U.S. PATENT DOCUMENTS

| | | |
|---|---|---|
| 2005/0137593 A1 | 6/2005 | Gray et al. |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biedermann et al. |
| 2005/0171543 A1 | 8/2005 | Timm et al. |
| 2005/0177154 A1 | 8/2005 | Moumene et al. |
| 2005/0177157 A1 | 8/2005 | Jahng |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192570 A1 | 9/2005 | Jackson |
| 2005/0192571 A1 | 9/2005 | Abdelgany |
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228385 A1 | 10/2005 | Iott et al. |
| 2005/0228400 A1 | 10/2005 | Chao et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0267577 A1 | 12/2005 | Trieu |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036255 A1 | 2/2006 | Pond et al. |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth et al. |
| 2006/0079899 A1 | 4/2006 | Ritland |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0095035 A1 | 5/2006 | Jones et al. |
| 2006/0095037 A1 | 5/2006 | Jones et al. |
| 2006/0106380 A1 | 5/2006 | Colleran et al. |

(56) References Cited

U.S. PATENT DOCUMENTS

| | | |
|---|---|---|
| 2006/0106381 A1 | 5/2006 | Ferree et al. |
| 2006/0106383 A1 | 5/2006 | Biedermann et al. |
| 2006/0106394 A1 | 5/2006 | Colleran |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0149251 A1 | 7/2006 | Ziolo et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann et al. |
| 2006/0184180 A1 | 8/2006 | Augostino et al. |
| 2006/0189983 A1 | 8/2006 | Fallin et al. |
| 2006/0189984 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195098 A1 | 8/2006 | Schumacher |
| 2006/0195198 A1 | 8/2006 | James |
| 2006/0200023 A1 | 9/2006 | Melkent et al. |
| 2006/0200123 A1 | 9/2006 | Ryan |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman et al. |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0217716 A1 | 9/2006 | Baker et al. |
| 2006/0229608 A1 | 10/2006 | Foster et al. |
| 2006/0229609 A1 | 10/2006 | Wang |
| 2006/0229612 A1 | 10/2006 | Rothman et al. |
| 2006/0229613 A1 | 10/2006 | Timm et al. |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241769 A1 | 10/2006 | Gordon et al. |
| 2006/0241771 A1 | 10/2006 | Gordon et al. |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247635 A1 | 11/2006 | Gordon et al. |
| 2006/0247636 A1 | 11/2006 | Yuan et al. |
| 2006/0247637 A1 | 11/2006 | Colleran et al. |
| 2006/0247658 A1 | 11/2006 | Pond et al. |
| 2006/0247779 A1 | 11/2006 | Gordon et al. |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0269940 A1 | 11/2006 | Li et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert et al. |
| 2006/0293657 A1 | 12/2006 | Hartmann |
| 2006/0293659 A1 | 12/2006 | Alvarez |
| 2006/0293663 A1 | 12/2006 | Walkenhorst et al. |
| 2006/0293665 A1 | 12/2006 | Shluzas |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016188 A1 | 1/2007 | Boehm et al. |
| 2007/0016190 A1 | 1/2007 | Martinez et al. |
| 2007/0016193 A1 | 1/2007 | Ritland |
| 2007/0016194 A1 | 1/2007 | Shaolian et al. |
| 2007/0016198 A1 | 1/2007 | Boehm et al. |
| 2007/0016199 A1 | 1/2007 | Boehm et al. |
| 2007/0021750 A1 | 1/2007 | Shluzas et al. |
| 2007/0032123 A1 | 2/2007 | Timm et al. |
| 2007/0043355 A1 | 2/2007 | Bette et al. |
| 2007/0043356 A1 | 2/2007 | Timm et al. |
| 2007/0043357 A1 | 2/2007 | Kirschman |
| 2007/0043358 A1 | 2/2007 | Molz et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055235 A1 | 3/2007 | Janowski et al. |
| 2007/0055236 A1 | 3/2007 | Hudgins et al. |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak et al. |
| 2007/0073290 A1 | 3/2007 | Boehm |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0073405 A1 | 3/2007 | Verhulst et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan et al. |
| 2007/0093814 A1 | 4/2007 | Callahan et al. |
| 2007/0093815 A1 | 4/2007 | Callahan et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |

(56) References Cited

U.S. PATENT DOCUMENTS

| | | |
|---|---|---|
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0124249 A1 | 5/2007 | Aerrabotu et al. |
| 2007/0129729 A1 | 6/2007 | Petit et al. |
| 2007/0135815 A1 | 6/2007 | Gerbec et al. |
| 2007/0156142 A1 | 7/2007 | Rezach et al. |
| 2007/0156237 A1 | 7/2007 | Kwak |
| 2007/0161986 A1 | 7/2007 | Levy |
| 2007/0161991 A1 | 7/2007 | Altarac et al. |
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0219554 A1 | 9/2007 | Landry et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0233155 A1 | 10/2007 | Lovell |
| 2007/0244481 A1 | 10/2007 | Timm |
| 2007/0250061 A1 | 10/2007 | Chin et al. |
| 2007/0260243 A1 | 11/2007 | Kagami |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0270869 A1 | 11/2007 | Young et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant et al. |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0114403 A1 | 5/2008 | Kuester et al. |
| 2008/0119849 A1 | 5/2008 | Beardsley et al. |
| 2008/0119850 A1 | 5/2008 | Sicvol et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154279 A1 | 6/2008 | Schumacher et al. |
| 2008/0154307 A1 | 6/2008 | Colleran et al. |
| 2008/0161854 A1 | 7/2008 | Bae et al. |
| 2008/0161857 A1 | 7/2008 | Hestad et al. |
| 2008/0161859 A1 | 7/2008 | Nilsson |
| 2008/0161863 A1 | 7/2008 | Arnold et al. |
| 2008/0167687 A1 | 7/2008 | Colleran et al. |

(56) References Cited

U.S. PATENT DOCUMENTS

| | | |
|---|---|---|
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0177332 A1 | 7/2008 | Reiley et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0221620 A1 | 9/2008 | Krause |
| 2008/0221692 A1 | 9/2008 | Zucherman et al. |
| 2008/0228184 A1 | 9/2008 | Hestad |
| 2008/0228227 A1 | 9/2008 | Brown et al. |
| 2008/0228228 A1 | 9/2008 | Hestad et al. |
| 2008/0228229 A1 | 9/2008 | Walder et al. |
| 2008/0234691 A1 | 9/2008 | Schwab |
| 2008/0234734 A1 | 9/2008 | Walder et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0234756 A1 | 9/2008 | Sutcliffe et al. |
| 2008/0234759 A1 | 9/2008 | Marino |
| 2008/0243052 A1 | 10/2008 | Pond et al. |
| 2008/0243185 A1 | 10/2008 | Felix et al. |
| 2008/0243188 A1 | 10/2008 | Walder et al. |
| 2008/0243194 A1 | 10/2008 | Lotz et al. |
| 2008/0249570 A1 | 10/2008 | Carson et al. |
| 2008/0249576 A1 | 10/2008 | Hawkes et al. |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262551 A1 | 10/2008 | Rice et al. |
| 2008/0262552 A1 | 10/2008 | Kim |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0269809 A1 | 10/2008 | Garamszegi |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0300630 A1 | 12/2008 | Bonnema et al. |
| 2008/0300633 A1 | 12/2008 | Jackson |
| 2008/0306513 A1 | 12/2008 | Winslow et al. |
| 2008/0306525 A1 | 12/2008 | Mitchell et al. |
| 2008/0306528 A1 | 12/2008 | Winslow et al. |
| 2008/0306533 A1 | 12/2008 | Winslow et al. |
| 2008/0306536 A1 | 12/2008 | Frigg et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow et al. |
| 2008/0312655 A1 | 12/2008 | Kirschman et al. |
| 2008/0312692 A1 | 12/2008 | Brennan et al. |
| 2008/0312694 A1 | 12/2008 | Peterman et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0005817 A1 | 1/2009 | Friedrich et al. |
| 2009/0012567 A1 | 1/2009 | Biedermann et al. |
| 2009/0018583 A1 | 1/2009 | Song et al. |
| 2009/0018591 A1 | 1/2009 | Hawkes et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1 | 1/2009 | Hestad et al. |
| 2009/0030465 A1 | 1/2009 | Altarac et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0054932 A1 | 2/2009 | Butler et al. |
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088782 A1 | 4/2009 | Moumene et al. |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad |
| 2009/0099599 A1 | 4/2009 | Biedermann et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0118772 A1 | 5/2009 | Diederich et al. |
| 2009/0125063 A1 | 5/2009 | Panjabi |
| 2009/0131981 A1 | 5/2009 | White |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0138056 A1 | 5/2009 | Anderson et al. |
| 2009/0143827 A1 | 6/2009 | Levy et al. |
| 2009/0143828 A1 | 6/2009 | Stad et al. |
| 2009/0143829 A1 | 6/2009 | Shluzas |
| 2009/0149885 A1 | 6/2009 | Durward et al. |
| 2009/0149887 A1 | 6/2009 | Schlaepfer et al. |
| 2009/0149892 A1 | 6/2009 | Stad et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0182380 A1 | 7/2009 | Abdelgany |
| 2009/0192548 A1 | 7/2009 | Jeon et al. |

(56) References Cited

U.S. PATENT DOCUMENTS

| | | |
|---|---|---|
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Mark et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2009/0326587 A1 | 12/2009 | Matthis et al. |
| 2010/0004692 A1 | 1/2010 | Biedermann et al. |
| 2010/0004695 A1 | 1/2010 | Stad et al. |
| 2010/0010540 A1 | 1/2010 | Park |
| 2010/0010544 A1 | 1/2010 | Fallin et al. |
| 2010/0016898 A1 | 1/2010 | Shluzas |
| 2010/0023061 A1 | 1/2010 | Randol et al. |
| 2010/0030224 A1 | 2/2010 | Winslow et al. |
| 2010/0030271 A1 | 2/2010 | Winslow et al. |
| 2010/0030272 A1 | 2/2010 | Winslow et al. |
| 2010/0030283 A1 | 2/2010 | King et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063550 A1 | 3/2010 | Felix et al. |
| 2010/0063551 A1 | 3/2010 | Richelsoph |
| 2010/0063552 A1 | 3/2010 | Chin et al. |
| 2010/0063553 A1 | 3/2010 | Warnick |
| 2010/0069919 A1 | 3/2010 | Carls et al. |
| 2010/0069963 A1 | 3/2010 | Eckman |
| 2010/0069964 A1 | 3/2010 | Lechmann |
| 2010/0069969 A1 | 3/2010 | Ampuero et al. |
| 2010/0087858 A1 | 4/2010 | Abdou |
| 2010/0087861 A1 | 4/2010 | Lechmann et al. |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0088782 A1 | 4/2010 | Oswald et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0114108 A1 | 5/2010 | Strauss |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121385 A1 | 5/2010 | Blain et al. |
| 2010/0121386 A1 | 5/2010 | Peultier et al. |
| 2010/0125302 A1 | 5/2010 | Hammill, Sr. et al. |
| 2010/0131017 A1 | 5/2010 | Farris et al. |
| 2010/0131018 A1 | 5/2010 | Konieczynski et al. |
| 2010/0137918 A1 | 6/2010 | Wilcox et al. |
| 2010/0137920 A1 | 6/2010 | Hammill, Sr. et al. |
| 2010/0145390 A1 | 6/2010 | McCarthy et al. |
| 2010/0152776 A1 | 6/2010 | Keyer et al. |
| 2010/0152785 A1 | 6/2010 | Forton et al. |
| 2010/0152787 A1 | 6/2010 | Walsh et al. |
| 2010/0152788 A1 | 6/2010 | Warnick |
| 2010/0160965 A1 | 6/2010 | Viker |
| 2010/0160974 A1 | 6/2010 | Viker |
| 2010/0160980 A1 | 6/2010 | Walsh et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0174326 A1 | 7/2010 | Selover et al. |
| 2010/0179602 A1 | 7/2010 | Dauster et al. |
| 2010/0179603 A1 | 7/2010 | Warnick |
| 2010/0185247 A1 | 7/2010 | Richelsoph |
| 2010/0191290 A1 | 7/2010 | Felix |
| 2010/0198261 A1 | 8/2010 | Trieu et al. |
| 2010/0198269 A1 | 8/2010 | Taylor et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0204736 A1 | 8/2010 | Biedermann et al. |
| 2010/0211104 A1 | 8/2010 | Moumene et al. |
| 2010/0222819 A1 | 9/2010 | Timm et al. |
| 2010/0222822 A1 | 9/2010 | Farris et al. |
| 2010/0222828 A1 | 9/2010 | Stad et al. |
| 2010/0228292 A1 | 9/2010 | Arnold et al. |
| 2010/0228293 A1 | 9/2010 | Courtney et al. |
| 2010/0234891 A1 | 9/2010 | Freeman et al. |
| 2010/0241170 A1 | 9/2010 | Cammisa et al. |
| 2010/0249843 A1 | 9/2010 | Wegrzyn, III |
| 2010/0249846 A1 | 9/2010 | Simonson |
| 2010/0249856 A1 | 9/2010 | Iott et al. |
| 2010/0256681 A1 | 10/2010 | Hammer et al. |
| 2010/0256682 A1 | 10/2010 | Fallin et al. |
| 2010/0262187 A1 | 10/2010 | Marik et al. |
| 2010/0262190 A1 | 10/2010 | Ballard et al. |

(56) References Cited

U.S. PATENT DOCUMENTS

| | | |
|---|---|---|
| 2010/0262196 A1 | 10/2010 | Barrus et al. |
| 2010/0274285 A1 | 10/2010 | Rouleau |
| 2010/0274287 A1 | 10/2010 | Rouleau et al. |
| 2010/0274288 A1 | 10/2010 | Prevost et al. |
| 2011/0015678 A1 | 1/2011 | Jackson |
| 2012/0078316 A1 | 3/2012 | Anderson et al. |
| 2014/0222082 A1 | 8/2014 | Jackson |
| 2014/0222092 A1 | 8/2014 | Anderson et al. |
| 2016/0000477 A1 | 1/2016 | Anderson et al. |
| 2017/0340368 A1 | 11/2017 | Anderson et al. |

FOREIGN PATENT DOCUMENTS

| | | |
|---|---|---|
| DE | 34 34 807 A1 | 12/1985 |
| DE | 92 02 745 U1 | 4/1992 |
| DE | 42 39 716 C1 | 8/1994 |
| DE | 44 25 392 A1 | 11/1995 |
| DE | 195 07 141 A1 | 9/1996 |
| DE | 195 09 141 A1 | 9/1996 |
| DE | 195 09 331 A1 | 9/1996 |
| DE | 298 06 563 U1 | 6/1998 |
| DE | 298 10 798 U1 | 10/1999 |
| DE | 199 51 145 A1 | 5/2001 |
| DE | 100 27 988 A1 | 1/2002 |
| DE | 202 07 850 U1 | 10/2002 |
| DE | 102 36 691 A1 | 2/2004 |
| DE | 10 2007 055 745 A1 | 7/2008 |
| EP | 0 528 562 A2 | 2/1993 |
| EP | 0 667 127 A1 | 8/1995 |
| EP | 0 669 109 A1 | 8/1995 |
| EP | 0 677 277 A2 | 10/1995 |
| EP | 0 885 598 A2 | 12/1998 |
| EP | 1 121 902 A2 | 8/2001 |
| EP | 1 190 678 A2 | 3/2002 |
| EP | 1 210 914 A1 | 6/2002 |
| EP | 1 570 795 A1 | 9/2005 |
| EP | 1 579 816 A1 | 9/2005 |
| EP | 1 634 537 A1 | 3/2006 |
| EP | 1 925 263 A1 | 5/2008 |
| FR | 2717370 A1 | 9/1995 |
| FR | 2718946 A1 | 10/1995 |
| FR | 2729291 A1 | 7/1996 |
| FR | 2796545 A1 | 1/2001 |
| FR | 2799949 A1 | 4/2001 |
| FR | 2814936 A1 | 4/2002 |
| FR | 2846223 A1 | 4/2004 |
| FR | 2856578 A1 | 12/2004 |
| FR | 2857850 A1 | 1/2005 |
| FR | 2865373 A1 | 7/2005 |
| FR | 2865375 A1 | 7/2005 |
| FR | 2865377 A1 | 7/2005 |
| FR | 2865378 A1 | 7/2005 |
| FR | 2925288 A1 | 6/2009 |
| GB | 1 519 139 A | 7/1978 |
| GB | 2 365 345 A | 2/2002 |
| GB | 2 382 304 A | 5/2003 |
| JP | 10-277070 A | 10/1998 |
| JP | 2000-325358 A | 11/2000 |
| SU | 313538 A3 | 10/1971 |
| WO | 89/12431 A1 | 12/1989 |
| WO | 91/16020 A1 | 10/1991 |
| WO | 92/03100 A1 | 3/1992 |
| WO | 92/05742 A1 | 4/1992 |
| WO | 93/08745 A1 | 5/1993 |
| WO | 93/21848 A1 | 11/1993 |
| WO | 94/10927 A1 | 5/1994 |
| WO | 94/10944 A1 | 5/1994 |
| WO | 94/26191 A1 | 11/1994 |
| WO | 94/28824 A2 | 12/1994 |
| WO | 95/13755 A1 | 5/1995 |
| WO | 95/31947 A1 | 11/1995 |
| WO | 96/06576 A1 | 3/1996 |
| WO | 96/21396 A1 | 7/1996 |
| WO | 96/28105 A1 | 9/1996 |
| WO | 96/28118 A1 | 9/1996 |
| WO | 96/41582 A1 | 12/1996 |
| WO | 97/14368 A1 | 4/1997 |
| WO | 97/27812 A1 | 8/1997 |
| WO | 98/01091 A1 | 1/1998 |
| WO | 98/15233 A1 | 4/1998 |
| WO | 98/25534 A1 | 6/1998 |
| WO | 98/32386 A1 | 7/1998 |
| WO | 98/34554 A1 | 8/1998 |
| WO | 98/38924 A2 | 9/1998 |
| WO | 99/05980 A1 | 2/1999 |
| WO | 99/38463 A2 | 8/1999 |
| WO | 99/47083 A1 | 9/1999 |
| WO | 00/22997 A1 | 4/2000 |
| WO | 00/27297 A1 | 5/2000 |
| WO | 00/65268 A1 | 11/2000 |
| WO | 00/66045 A1 | 11/2000 |
| WO | 01/10317 A1 | 2/2001 |
| WO | 01/15612 A1 | 3/2001 |
| WO | 01/28435 A1 | 4/2001 |
| WO | 01/28436 A1 | 4/2001 |
| WO | 01/45576 A1 | 6/2001 |
| WO | 01/49191 A1 | 7/2001 |
| WO | 01/67972 A2 | 9/2001 |
| WO | 01/67974 A1 | 9/2001 |
| WO | 02/34150 A2 | 5/2002 |
| WO | 02/054966 A2 | 7/2002 |
| WO | 02/102259 A2 | 12/2002 |
| WO | 03/007828 A1 | 1/2003 |
| WO | 03/026523 A1 | 4/2003 |
| WO | 03/047442 A1 | 6/2003 |
| WO | 03/068088 A1 | 8/2003 |
| WO | 2004/017847 A2 | 3/2004 |
| WO | 2004/022108 A2 | 3/2004 |
| WO | 2004/041100 A1 | 5/2004 |
| WO | 2004/075778 A2 | 9/2004 |
| WO | 2004/089245 A2 | 10/2004 |
| WO | 2004/098452 A2 | 11/2004 |
| WO | 2004/107997 A2 | 12/2004 |
| WO | 2005/000136 A1 | 1/2005 |
| WO | 2005/000137 A1 | 1/2005 |
| WO | 2005/013839 A2 | 2/2005 |
| WO | 2005/018466 A2 | 3/2005 |
| WO | 2005/020829 A1 | 3/2005 |
| WO | 2005/030068 A1 | 4/2005 |
| WO | 2005/041799 A1 | 5/2005 |
| WO | 2005/065374 A2 | 7/2005 |
| WO | 2005/065375 A2 | 7/2005 |
| WO | 2005/072632 A1 | 8/2005 |
| WO | 2005/082262 A2 | 9/2005 |
| WO | 2005/087121 A1 | 9/2005 |
| WO | 2005/099400 A2 | 10/2005 |
| WO | 2005/102195 A1 | 11/2005 |
| WO | 2005/104969 A1 | 11/2005 |
| WO | 2006/005198 A1 | 1/2006 |
| WO | 2006/012088 A1 | 2/2006 |
| WO | 2006/017616 A1 | 2/2006 |
| WO | 2006/020530 A2 | 2/2006 |
| WO | 2006/028537 A2 | 3/2006 |
| WO | 2006/042188 A2 | 4/2006 |
| WO | 2006/045094 A2 | 4/2006 |
| WO | 2006/047711 A2 | 5/2006 |
| WO | 2006/066685 A1 | 6/2006 |
| WO | 2006/079531 A1 | 8/2006 |
| WO | 2006/086537 A2 | 8/2006 |
| WO | 2006/096240 A2 | 9/2006 |
| WO | 2006/096351 A1 | 9/2006 |
| WO | 2006/104874 A2 | 10/2006 |
| WO | 2006/110463 A1 | 10/2006 |
| WO | 2006/116662 A1 | 11/2006 |
| WO | 2006/119241 A2 | 11/2006 |
| WO | 2007/002409 A2 | 1/2007 |
| WO | 2007/118045 A2 | 10/2007 |
| WO | 2007/124222 A1 | 11/2007 |
| WO | 2007/130835 A2 | 11/2007 |
| WO | 2007/130840 A1 | 11/2007 |
| WO | 2007/130941 A2 | 11/2007 |
| WO | 2008/045210 A2 | 4/2008 |
| WO | 2008/069420 A1 | 6/2008 |
| WO | 2008/088731 A1 | 7/2008 |

(56) References Cited

FOREIGN PATENT DOCUMENTS

| WO | 2008/088990 A2 | 7/2008 |
|----|----------------|--------|
| WO | 2008/089075 A1 | 7/2008 |
| WO | 2008/140756 A2 | 11/2008 |
| WO | 2009/015100 A2 | 1/2009 |
| WO | 2009/036541 A2 | 3/2009 |
| WO | 2009/152302 A1 | 12/2009 |
| WO | 2010/018316 A1 | 2/2010 |
| WO | 2010/018317 A1 | 2/2010 |
| WO | 2010/019704 A1 | 2/2010 |
| WO | 2010/019857 A2 | 2/2010 |

OTHER PUBLICATIONS

[No Author Listed] The Dilation Retractor System. Product Literature (4 pages) Bright Medical Instruments, Boca Raton, FL (Apr. 2001).

Search Report from related EP 04 81 2446 dated Dec. 2, 2008.

Foley, Kevin T., "CD Horizon SEXTANT Rod Insertion System Surgical Technique" Medtronic Sofamor Danek Product Brochure (32 pages) Jul. 2002.

Jampel, Robert and Charles Bloomgarden. "Individual extraocular muscle function from faradic stimulation of the oculomotor and trochlear nerves of the macaque," Investigative Opthamology, Jun. 1963, 265-266.

Muller, et al., "A Keyhole Approach for Endoscopically Assisted Pedicle Screw Fixation in Lumbar Spine Instability," Neurosurgery, vol. 47, No. 1, Jul. 2000.

Speer, et al., "An Arthroscopic Technique for Anterior Stabiliatin of the Shoulder with a Bioabsorbable Tack," J. Bone Joint Surg Am. 1996; 78:1801-7.

Wiltse LL and Spencer, CW, "New Uses and Refinements of the Paraspinal Approach," Jun. 6, 1988, Lippincott Williams and Wilkins, SPINE Jun. 1988;13(6):696-706.

[No Author Listed] Blackstone Spinal Fixation System, The Strength of Innovation, Advertisement, Blackstone Medical Inc., publication date is unknown. 1 page.

[No Author Listed] Brochure of Spinal Concepts, An Abbott Laboratories Company, PathFinder, Minimally Invasive Pedicle Fixation System, Publication Date : Nov. 2003. 4 pages.

[No Author Listed] Brochure of Spinal Concepts, InCompass, Thoracolumbar Fixation System, Publication Date : Oct. 2003. 4 pages.

[No Author Listed] Brochure of Spinal Concepts, PathFinder, Minimally Invasive Pedicle Fixation System, Publication Date: May 2003. 4 pages.

[No Author Listed] Brochure of Spinal Concepts, Surgical Technique, InCompass, Thoracolumbar Fixation System, Publication Date : Oct. 2003. 18 pages.

[No Author Listed] CD Horizon M8 Multi Axial Screw Spinal System, Brochure, Medtronic Sofamor Danek, Publication date is unknown. 4 pages.

[No Author Listed] Claris Instrumentation, Brochure, Eurosurgical Ltd., pub. 1997. 6 pages.

[No Author Listed] Contour Spinal System Brochure, Ortho Development Corporation, Publication date is unknown, 1 page.

[No Author Listed] EBI Omega 21(TM), Versatile System Adapts to Virtually Any Anatomical Need, Brochure, EBI, L.P., pub. 1999. 1 page.

[No Author Listed] Moss Miami 6.0mm System, and Moss Miami 4.0mm Sytem, Advertisement, publication date is unknown, 1 page.

[No Author Listed] SDRS (TM) Surgical Dynamics Rod System, Brochure, Surgical Dynamics, Inc., pub. 1998-99. 11 pages.

[No Author Listed] Silhouette Spinal Fixation System, Brochure, Sulzer Medica Spine-Tech, publication date is unknown. 7 pages.

[No Author Listed] Spiral Radius 90D (TM), Brochure of Tyco/Healthcare/Surgical Dynamics, Inc., Publication Date: Sep. 2001, pp. 1-8.

[No Author Listed] Surgical Technique, Expedium (TM) Spine System, Brochure of DePuy Spine, Inc., Published 2004, pp. 1-36.

[No Author Listed] The Rod Plate System, Brochure, Stryker Spine, pub. Oct. 1999. 6 pages.

[No Author Listed] Versalok (R) Low Back Fixation System, Technical Monograph, Brochure, Wright Medical Technology, Inc., publ. 1997. 6 pages.

[No Author Listed] VLS (TM) System Variable Locking Screw, Brochure, Interpore Cross International, 1999. 4 pages.

[No Author Listed] Xia Spinal System, Brochure, Stryker Howmedica Osteonics, Stryker Spine, publication date is unknown, 26 pages.

Davis, R.J., MD, Facs, et al., Brochure of Zimmer Spine, Inc., Dynesys (R) LIS Less Invasive Surgery, The Dynamic Stabilization System, Publication Date: 2005. 23 pages.

European Search Report, EP14189707.4, dated Feb. 25, 2015. (13 pages).

Khoo, L.T., MD, et al., Minimally Invasive Posterior Spinal Decompression and Fusion Procedures, Brochure of SpineLine, Current Concepts, Publication Date: Sep./Oct. 2003, pp. 9-18.

Simmons, E.H., MD, et al., Brochure of Sofamor Danek the Spine Specialist, TSRH, Pedicle Screw Spinal System, Publication Date : Jan. 23, 1995. 27 pages.

* cited by examiner

METHODS AND DEVICES FOR MINIMALLY INVASIVE SPINAL FIXATION ELEMENT PLACEMENT

CROSS REFERENCE TO RELATED APPLICATIONS

The present application is a continuation of U.S. application Ser. No. 14/853,093 filed on Sep. 14, 2015, which is a continuation of U.S. application Ser. No. 14/251,467 filed on Apr. 11, 2014, which is a continuation of U.S. application Ser. No. 13/309,944 filed on Dec. 2, 2011, which is a continuation of U.S. application Ser. No. 12/365,711 filed on Feb. 4, 2009, which is a divisional of U.S. application Ser. No. 10/738,130 filed on Dec. 16, 2003. These references are hereby incorporated by reference in their entireties.

FIELD OF THE INVENTION

This application relates to tools for use in spinal surgery, and in particular to minimally invasive methods and devices for introducing a spinal fixation element to one or more spinal anchor sites within a patient's spine.

BACKGROUND OF THE INVENTION

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive devices and methods for implanting spinal fixation devices. One such method, for example, is disclosed in U.S. Pat. No. 6,530,929 of Justis et al. and it utilizes two percutaneous access devices for implanting an anchoring device, such as a spinal screw, into adjacent vertebrae. A spinal rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle. Moreover, the use of three separate access sites can undesirably lengthen the surgical procedure, and increase patient trauma and recovery time.

Accordingly, there remains a need for improved minimally invasive devices and methods for introducing a spinal fixation element into a patient's spine.

SUMMARY OF THE INVENTION

The present invention provides minimally invasive methods and devices for delivering a spinal fixation element to one or more spinal anchor sites in a patient's spinal column. In one embodiment, a spinal anchor is percutaneously delivered to a vertebral body with a percutaneous access device mated thereto and having a lumen extending therethrough and defining a longitudinal axis. A spinal fixation element is then advanced through the lumen in the percutaneous access device in a first, lengthwise orientation in which the fixation element is substantially parallel to the longitudinal axis of the percutaneous access device. The spinal fixation element can then be manipulated to extend in a second orientation, such that the fixation element is angled with respect to the first orientation, to position the spinal fixation element in relation to the spinal anchor. The method can also include the step of percutaneously delivering a second spinal anchor to a vertebral body with a second percutaneous access device mated thereto. The spinal fixation element thus preferably extends between the first and second spinal anchors in the second orientation.

In an exemplary embodiment, the percutaneous access device is in the form of an elongate, generally cylindrical tube that is adapted for percutaneous delivery and that is adapted to mate to a spinal anchor. The tube can include proximal and distal ends with a lumen extending therebetween. The lumen is adapted to transport a spinal fixation element therethrough in a first, lengthwise orientation that is substantially parallel to a longitudinal axis of the percutaneous access device, and to deliver the spinal fixation element to a spinal anchor site in a second orientation that is angled with respect to the first orientation, and more preferably that is substantially parallel to a patient's spinal column. The percutaneous access device can also include at least one sidewall opening extending from the distal end of the elongate, generally cylindrical tube through at least a portion thereof for facilitating transition of a spinal fixation element from the first orientation to the second orientation. In one embodiment, the device includes opposed sidewall openings formed therein adjacent to the distal end thereof. The device can also optionally or alternatively include a guide member formed within the lumen that is adapted to direct a spinal fixation element disposed therein from the first orientation to the second orientation. The guide member can be, for example, a sloped shelf formed within the lumen of the percutaneous access device.

In another embodiment of the present invention, a minimally invasive method for delivering a spinal fixation element to a spinal anchor site in a patient's spinal column is provided. The method includes the step of introducing a spinal fixation element into a lumen of a percutaneous access device. The lumen preferably forms a pathway to a spinal anchor disposed in a patient's vertebra. In an exemplary embodiment, the percutaneous access device has an outer diameter that is substantially the same as or less than a largest width of the spinal anchor to which it is attached. A person skilled in the art will appreciate that the outer diameter of the percutaneous access device can optionally be greater than the outer diameter of the spinal anchor to which it is attached. The method further includes the steps of advancing the spinal fixation element distally through the lumen in a first, lengthwise orientation that is substantially parallel to a longitudinal axis of the percutaneous access device, and manipulating the spinal fixation element into a second orientation that is substantially parallel to the patient's spinal column. The spinal fixation element can then be positioned relative to one or more spinal anchors.

In other aspects of the present invention, a minimally invasive surgical method is provided that includes the steps of making a first percutaneous incision in a patient, and creating a first pathway from the first percutaneous incision to an anchor site on a first vertebral body. Preferably, the pathway is a minimally invasive pathway such that it leads only to a single anchor site, rather than multiple anchor sites. This can be achieved, for example, by a percutaneous access device that has a substantially uniform width from the first percutaneous incision to a first anchor site on a first vertebral body. In an exemplary embodiment, the first pathway has a width that is substantially equal to or less than a width of the first percutaneous incision, and/or that is substantially equal to or less than a width of a first anchor. The method also includes the steps of placing a first anchor through the first percutaneous incision, advancing the first anchor along the first pathway to the single anchor site, and placing a fixation element through the first pathway in an orientation substantially parallel to a longitudinal axis of the first pathway.

In a further embodiment, a second percutaneous incision can be made in a patient, and a second minimally invasive pathway can be created from the second percutaneous incision to a second anchor site on a second vertebral body. A second anchor is then advanced along the second pathway to the second anchor site on the second vertebral body.

Additional methods and devices for introducing a spinal fixation element to one or more spinal anchor sites are also provided.

DETAILED DESCRIPTION OF THE INVENTION

The present invention provides minimally invasive methods and devices for introducing a spinal fixation element into a surgical site in a patient's spinal column. In general, the method involves advancing a spinal fixation element in a lengthwise orientation along a minimally invasive pathway that extends from a minimally invasive percutaneous incision to a spinal anchor site. In an exemplary embodiment, a percutaneous access device is used to create the minimally invasive pathway for receiving the spinal fixation element and for delivering the fixation element to a spinal anchor site. The spinal fixation element is preferably inserted through a lumen in the percutaneous access device in a lengthwise orientation, such that the spinal fixation element is oriented substantially parallel to a longitudinal axis of the percutaneous access device. As the spinal fixation element approaches or reaches the distal end of the pathway, the spinal fixation element can be manipulated to orient it at a desired angle with respect to the percutaneous access device, preferably such that the spinal fixation element is substantially parallel to the patient's spinal column. The spinal fixation element can then optionally be positioned to couple it, either directly or indirectly, to one or more spinal anchors. A fastening element or other closure mechanism, if necessary, can then be introduced into the spinal anchor site to fixedly mate the spinal fixation element to the anchor(s).

The methods and devices of the present invention are particularly advantageous in that they can be achieved using one or more minimally invasive percutaneous incisions for accessing the spinal column. Such incisions minimize damage to intervening tissues, and they reduce recovery time and post-operative pain. The present invention also advantageously provides techniques for delivering spinal fixation elements and anchors along a minimally invasive pathway, thus eliminating the need to create a large working area at the surgical site.

Figure 1:
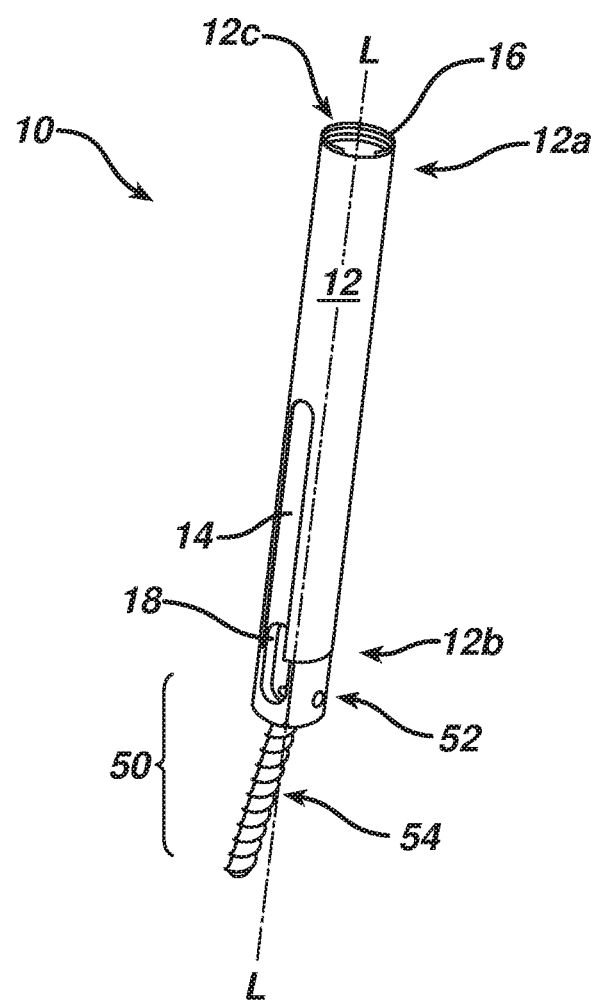
FIG. 1 is a perspective view of a percutaneous access device coupled to an anchor according to one embodiment of the present invention.
Figure 2:
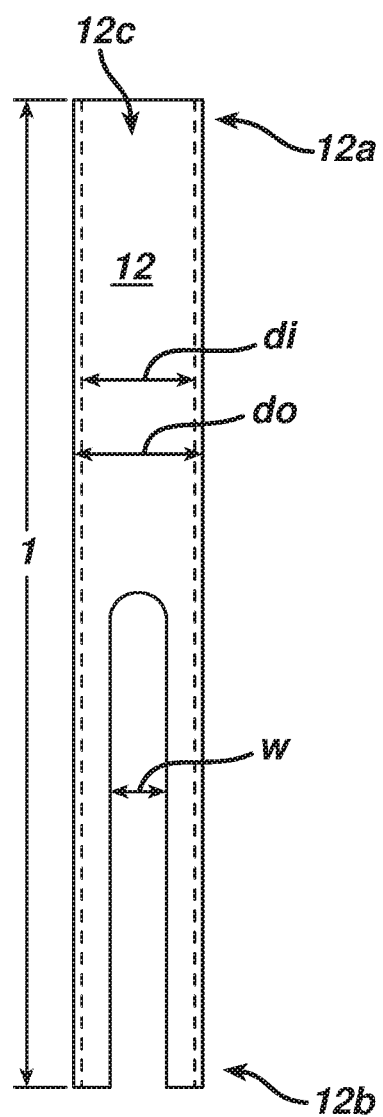
FIG. 2 is a cross-sectional view taken along the longitudinal axis of the percutaneous access device shown in FIG. 1.

While a variety of devices can be used to perform the methods of the present invention, FIGS. 1 and 2 illustrate an exemplary embodiment of a percutaneous access device 12 that is mated to a spinal anchor 50 (FIG. 1) to form a spinal implant assembly 10. As shown, the device 12 is in the form of a generally elongate, cylindrical tube having an inner lumen 12c formed therein and defining a longitudinal axis L that extends between proximal and distal ends 12a, 12b. The size of the access device 12 can vary depending on the intended use, but it should have a length l that allows the proximal end 12a of the access device 12 to be positioned outside the patient's body, while the distal end 12b of the access device 12 is coupled to, or positioned adjacent to, a spinal anchor, e.g., anchor 50, that is disposed in a vertebra in a patient's spine. The access device 12 is also preferably adapted to provide a minimally invasive pathway for the delivery of a spinal fixation element, and in particular, the percutaneous access device 12 should also be adapted to be implanted through a minimally invasive percutaneous incision, which is a relatively small incision that typically has a length that is less than a diameter or width of the device being inserted therethrough.

In an exemplary embodiment, the device 12 has an inner diameter $d_i$ that is sufficient to allow a spinal fixation element to be introduced therethrough, preferably in a lengthwise orientation. The inner diameter $d_i$ can also optionally be configured to allow a driver mechanism to be introduced therethrough for applying a closure mechanism to lock the spinal fixation element in relation to a spinal anchor. The outer diameter $d_o$ of the access device 12 can also vary, and it can be the same as, less than, or greater than an outer diameter $d_r$ of the spinal anchor. In the illustrated embodiment, the access device 12 has an outer diameter $d_o$ that is substantially the same as an outer diameter $d_r$ of the spinal anchor, which, as illustrated in FIG. 1, is the receiver head 52 of a spinal screw 50. This is particularly advantageous in that the size of the incision does not need to be any larger than necessary. The matching outer diameters $d_o$, $d_r$ of the access device 12 and the anchor 50 also allow the access device 12 and/or the anchor 50 to be introduced through a cannula. If the access device 12 is mated to the anchor 50, the matching outer diameters $d_o$, $d_r$ also allows a sleeve or other device to be slidably disposed therearound to prevent disengagement between the access device 12 and the anchor 50. In another, exemplary embodiment, the outer diameter $d_o$ of the access device 12 can be slightly greater than the outer diameter $d_r$ of the spinal anchor. By way of non-limiting example, where a receiver head of the spinal anchor has an outer diameter $d_r$ that is about 13 mm, the access device 12 preferably has an outer diameter $d_o$ that is about 15 mm.

The percutaneous access device 12 also preferably includes at least one sidewall opening or slot 14 formed therein, and more preferably it includes two opposed sidewall openings (only one opening 14 is shown) formed therein and extending proximally from the distal end 12b thereof. The openings 14 allow a spinal fixation element to be introduced through the device 12 in a first, lengthwise orientation, in which the spinal fixation element is substantially parallel to the longitudinal axis L of the access device 12. The spinal fixation element can then to be manipulated to extend at an angle with respect to the first orientation, such that the fixation element extends in a direction substantially transverse to the longitudinal axis L of the access device 12, for example, in a direction that is substantially parallel to the patient's spine. Since the length L of the spinal fixation element will necessarily be greater than the inner diameter $d_i$ of the access device 12, the openings 14 allow the spinal fixation element to pass therethrough while being transitioned from the first, lengthwise orientation to the second orientation. A person skilled in the art will appreciate that the exact position of the spinal fixation element with respect to the longitudinal axis L will of course vary depending on the configuration of the spinal fixation element.

The shape and size of each opening 14 can vary, but the opening(s) 14 should be effective to allow movement of the spinal fixation element from the first orientation to the second orientation. In an exemplary embodiment, the openings 14 extend over about half of the length, or less than half of the length, of the percutaneous access device 12. The shape of each slot 14 can be generally elongate, and they should each have a width w that is sufficient to accommodate the diameter of the spinal fixation element. A person skilled in the art will appreciate that the percutaneous access device 12 can include any number of sidewall openings having any shape that is sufficient to allow a spinal fixation element to be moved from the first orientation to the second orientation.

Figure 3A:
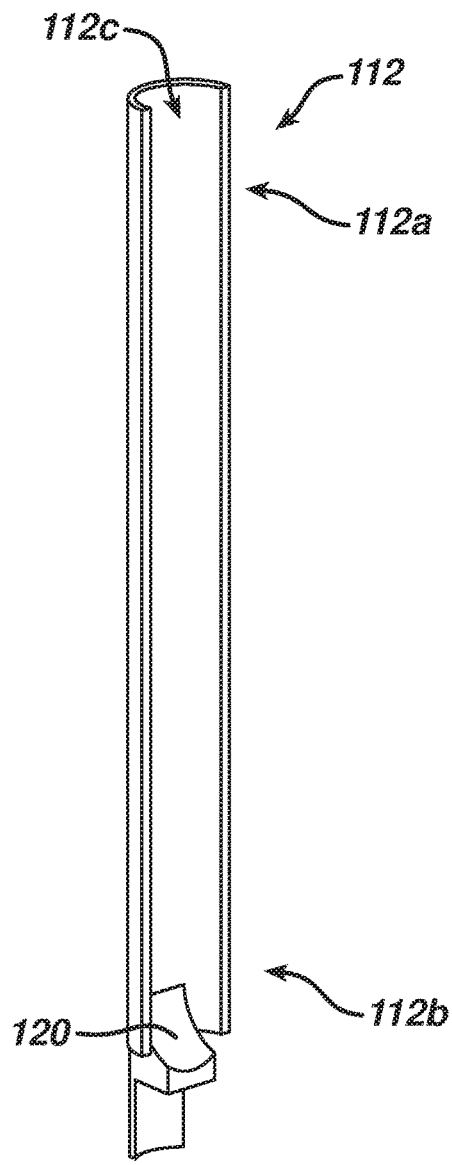
FIG. 3A is a partially cut-away view of another embodiment of a percutaneous access device having a guide member formed therein.
Figure 3B:
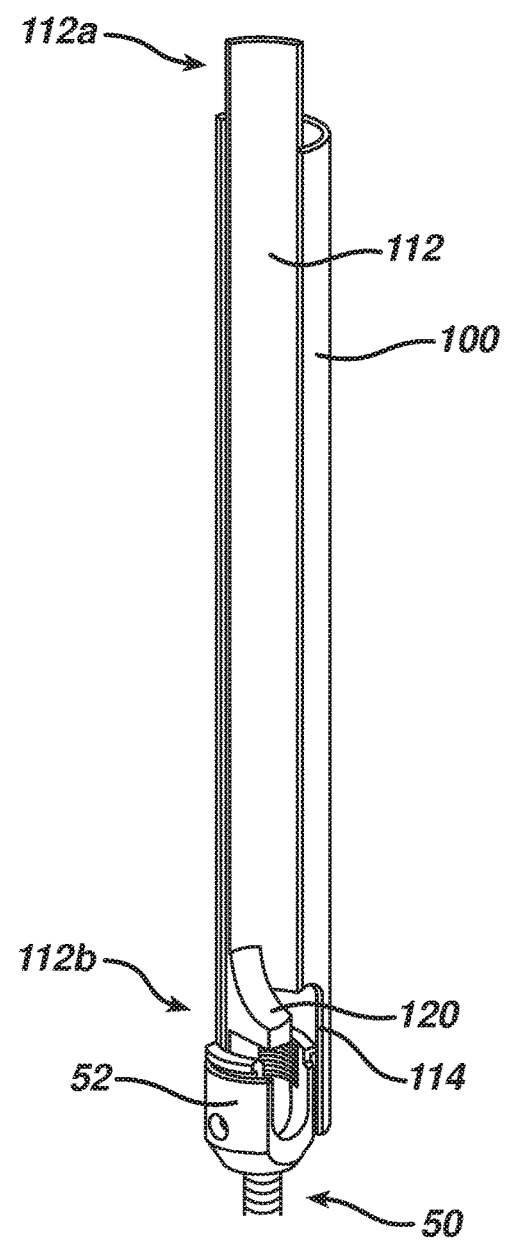
FIG. 3B is a partially cut-away view of the percutaneous access device shown in FIG. 3A having a sleeve disposed therearound and a spinal anchor mated thereto.

In another embodiment of the present invention, shown in FIGS. 3A-3B, the percutaneous access device 112 can also optionally include a guide member 120 formed within the distal end 112b of the lumen 112c to help guide the spinal fixation element from the first orientation to the second orientation. The guide member 120 can have a variety of configurations, but it should be effective to guide the spinal fixation element from the first orientation toward the anchor 50 attached to, or positioned adjacent to, the access device 112, and optionally toward anchor(s) implanted in adjacent vertebrae. In an exemplary embodiment, as shown, the guide member 120 is in the form of a sloped shelf formed within the inner lumen 112c of the access device 112 and preferably positioned opposite to a single sidewall slot 114 formed in the access device 112. The sloped shelf 120 can vary in shape and size depending on the type of fixation element being used and/or the geometry of the access device. In use, as the leading end of a spinal fixation element, such as a spinal rod, contacts the shelf 120, the shelf 120 begins to direct the spinal fixation element into the second orientation, thereby causing the spinal fixation element to extend in a direction that is substantially transverse to the axis L of the device 112, and that is preferably substantially parallel to the patient's spinal column. The spinal fixation element can then be manipulated to position it in relation to one or more spinal anchors, as will be discussed in more detail below.

Referring back to FIG. 1, in use, the percutaneous access device 12 can be adapted to attach to a spinal anchor 50. Accordingly, the distal end 12*c* of the percutaneous access device 12 can include one or more mating elements 18 formed thereon or therein for engaging the anchor 50. Suitable mating elements include, for example, threads, a twist-lock engagement, a snap-on engagement, or any other technique known in the art, and in an exemplary embodiment the mating elements are formed on opposed inner surfaces of the distal end 12*b* of the access device 12. A sleeve 100 (partially shown in FIG. 3B) or other device, preferably having sidewall openings (not shown) that correspond with the sidewall openings 14 formed in the percutaneous access device 12, can also be placed over the percutaneous access device 12, and optionally over the implant 50 as well, to prevent disengagement of the access device 12 from the implant 50 during use. Exemplary techniques for mating the percutaneous access device 12 to an anchor are disclosed in U.S. application Ser. No. 10/738, 286 entitled "Percutaneous Access Devices and Bone Anchor Assemblies," filed on Dec. 16, 2003 (now U.S. Pat. No. 7,179,261). A person skilled in the art will appreciate that a variety of other techniques can be used to removably mate the percutaneous access device to an anchor.

For reference purposes, FIG. 1 illustrates an exemplary spinal anchor for use with the methods and devices of the present invention. A person skilled in the art will appreciate that a variety of anchors can be used with the devices and methods of the present invention, including, for example, spinal screws, hooks, bolts, and wires. FIG. 1 illustrates a spinal screw that includes a distal, bone-engaging portion, e.g., a threaded shank 54, and a proximal, U-shaped, receiver head 52 that is adapted to seat a spinal fixation element, preferably a spinal rod (not shown). The threaded shank 54 can be fixedly attached to the receiver head 52 to form a monoaxial screw, or alternatively the shank 54 can be configured as a polyaxial screw, as shown, that is rotatably disposed through an opening formed in the distal end of the receiver head 52 to allow rotation of the shank 54 with respect to the receiver head 52. A variety of techniques can be used to allow rotation of the head 52 with respect to the shank 54.

FIGS. 4A-17 show a minimally invasive method of implanting a spinal fixation element. While the method is shown and described in connection with the percutaneous access device 12 and spinal screw 50 disclosed herein, a person skilled in the art will appreciate that the method is not limited to use with such devices, and that a variety of other devices known in the art can be used. Moreover, while only two access devices 12, 12' and two anchors 50, 50' are shown in FIGS. 4-14, the method of the present invention can be performed using any number of access devices and anchors. The method can also be performed using only some of the method steps disclosed herein, and/or using other methods known in the art.

Figure 4A:
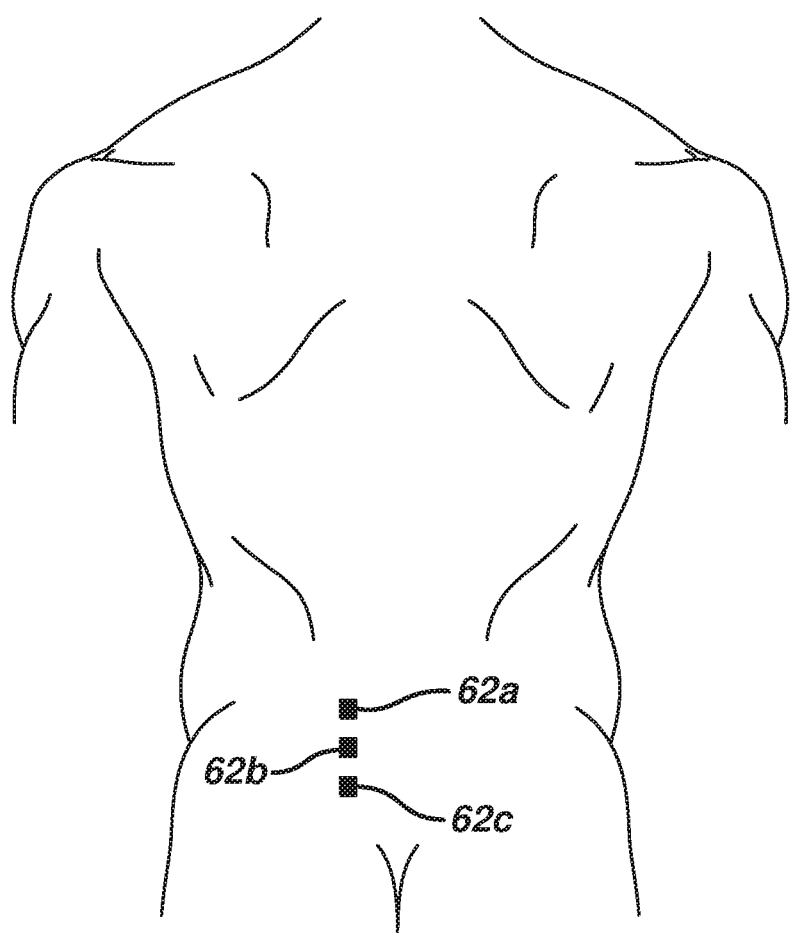
FIG. 4A is a posterior view of three percutaneous incisions formed in the thoracolumbar fascia of a patient's back.
Figure 4B:
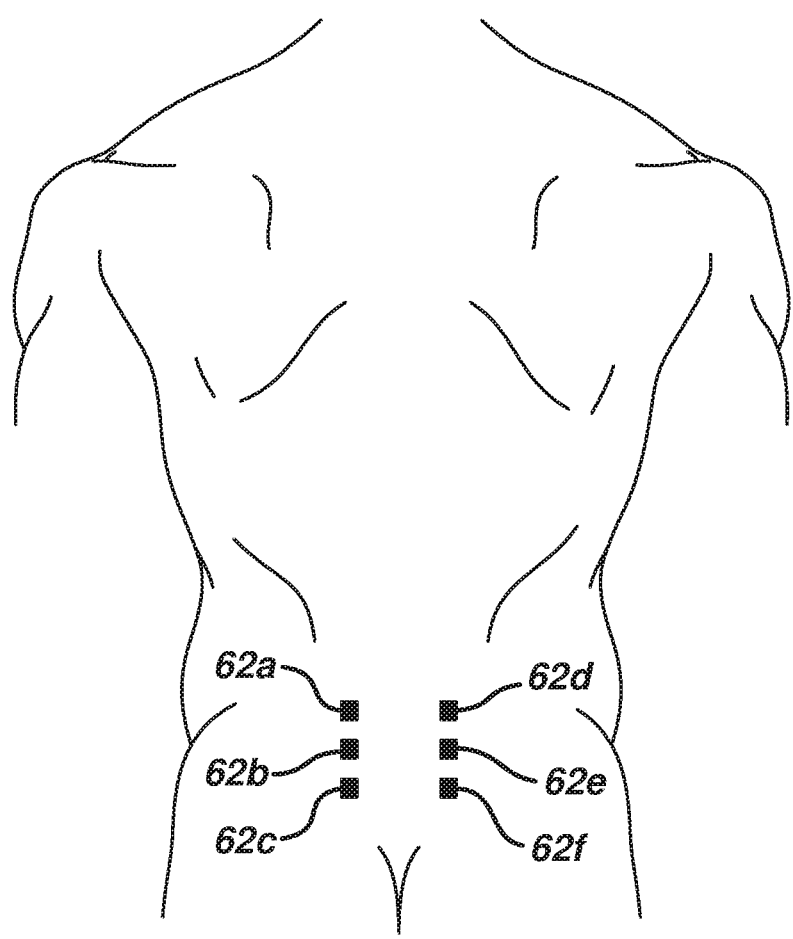
FIG. 4B is a posterior view of six percutaneous incisions formed in the thoracolumbar fascia of a patient's back.
Figure 5A:
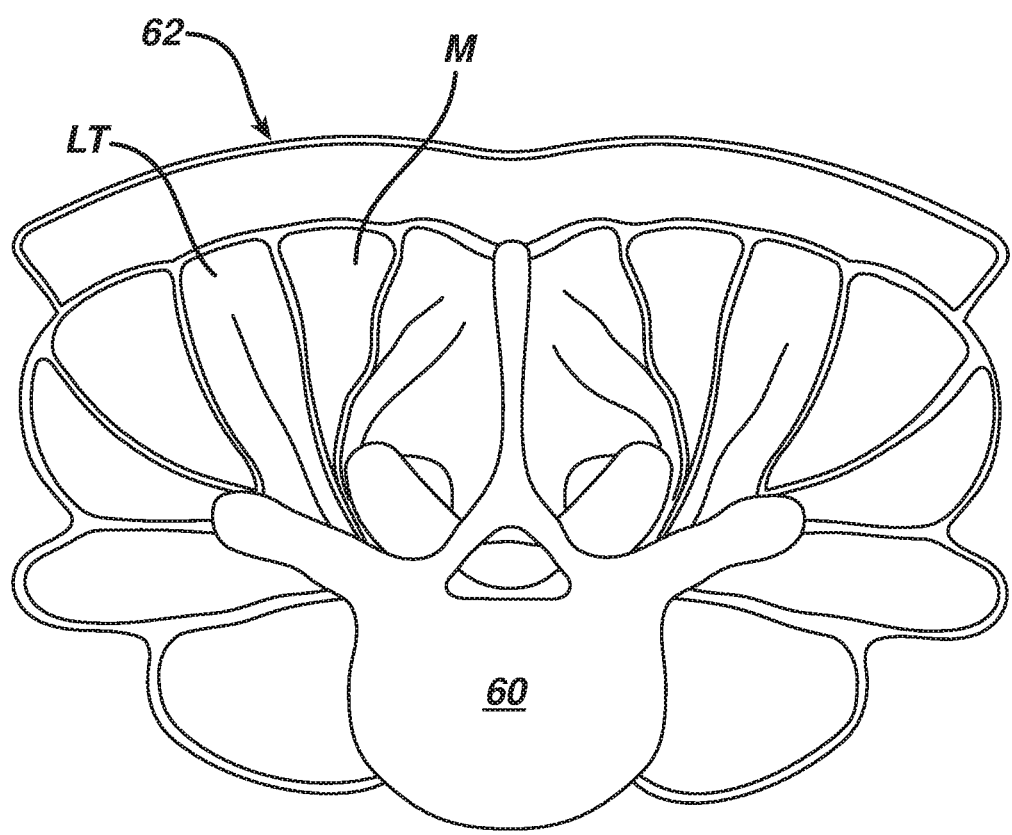
FIG. 5A is an end view showing a blunt dissection of the muscles surrounding a patient's vertebra.
Figure 5B:
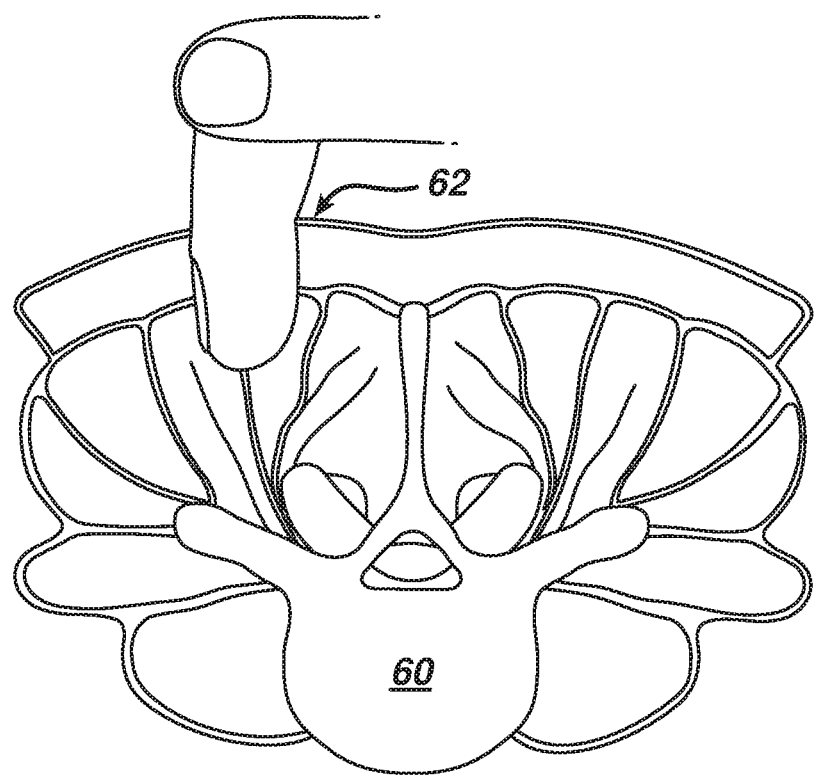
FIG. 5B is an end view of the vertebra shown in FIG. 5A showing a technique for separating the muscles along the dissection muscle plane to gain access to the vertebra.

The procedure preferably begins by forming a minimally invasive percutaneous incision through the tissue located adjacent to the desired implant site. While the location, shape, and size of the incision will depend on the type and quantity of spinal anchors being implanted, FIG. 4A illustrates three midline minimally invasive percutaneous incisions 62*a*-*c* formed on one side of three adjacent vertebra in the thoracolumbar fascia in the patient's back, and FIG. 4B illustrates three additional midline minimally invasive percutaneous incisions 62*d*-*f* formed on the opposite side of the three adjacent vertebra in the thoracolumbar fascia in the patient's back. Each incision 62*a*-*f* is a stab incision that has a diameter of about 10-20 mm in diameter, however this can vary depending on the procedure. In an exemplary embodiment, each incision 62*a*-*f* has a diameter that is equal to or less than a largest diameter of the anchor and/or the percutaneous access device being inserted therethrough. While probably not necessary, once the percutaneous incisions 62*a*-*f* are formed, blunt finger dissection can optionally be used, as shown in FIG. 5A-5B, to separate the longissimus thoracis and multifidus muscles, thereby exposing the facet and the junction of the transverse process and superior articular process.

Figure 6:
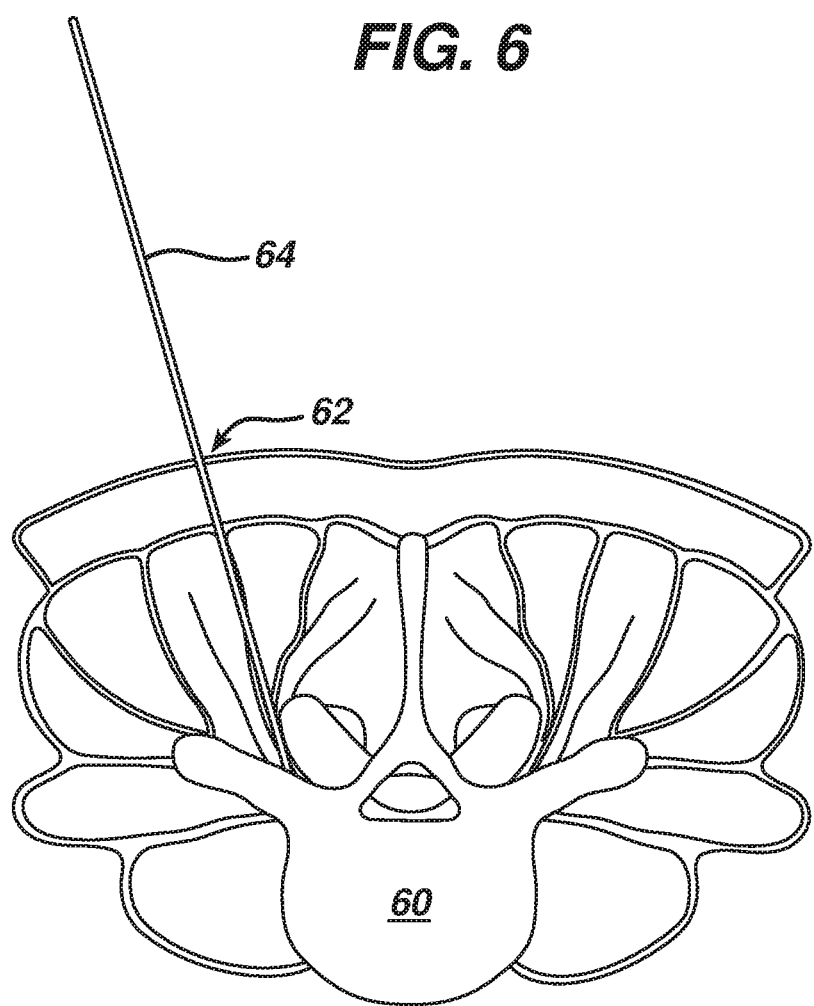
FIG. 6 is an end view of the vertebra shown in FIG. 4 showing placement of a k-wire through the incision and into the patient's vertebra.

As shown in FIG. 6, a guide wire, e.g., a k-wire 64, can be implanted, either prior to or after formation of the incision, at each spinal anchor implant site. The k-wire 64 preferably extends between the muscles and into the vertebra at the desired entry point of the spinal anchor. Fluoroscopy is typically used to facilitate proper placement of the k-wire 64.

Figure 7:
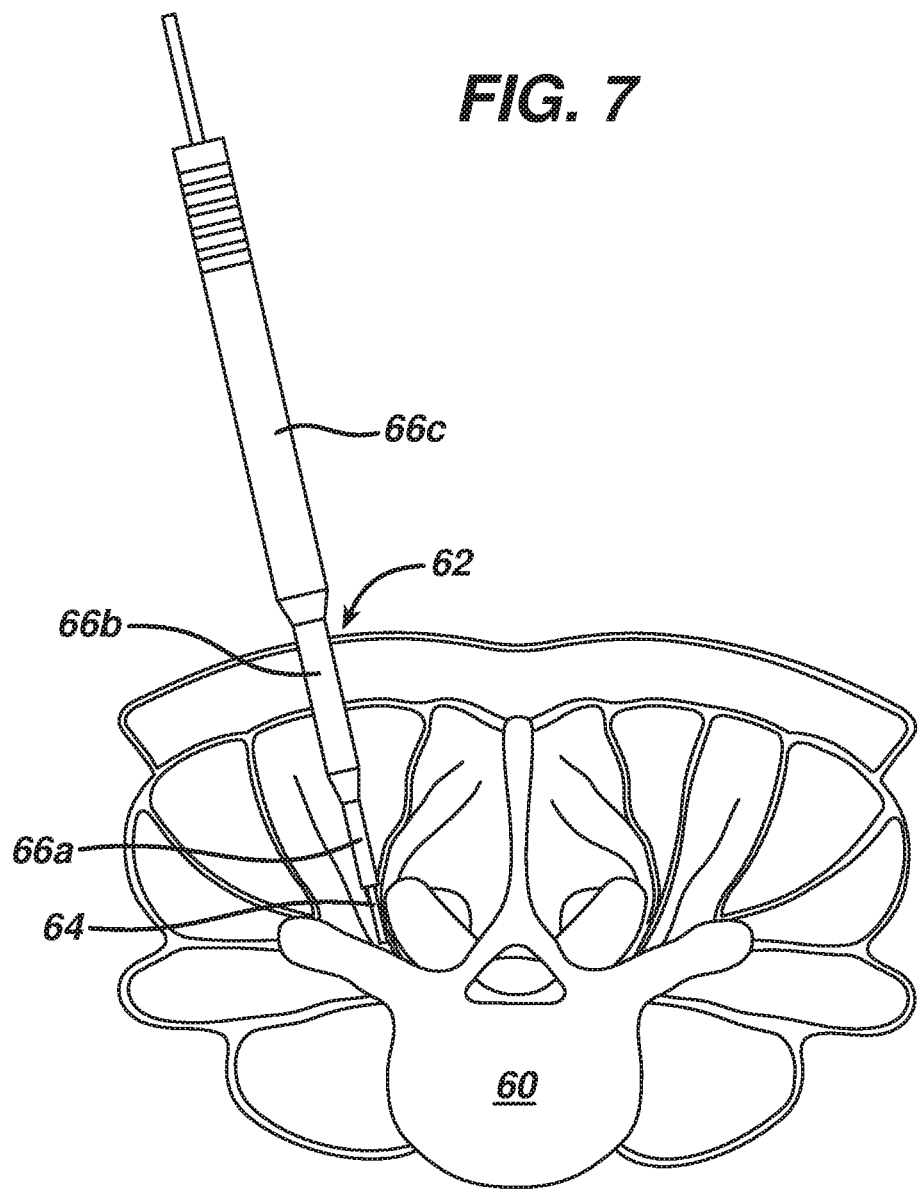
FIG. 7 is an end view of the vertebra shown in FIG. 6 having an obturator and several dilators disposed over the k-wire to dilate the tissue and muscles.

The opposed ends of the incision can then be dilated to provide a pathway for delivery of a spinal anchor to each implant site. FIG. 7 illustrates dilation at one end of the incision 62 using an obturator 66*a* having several dilators 66*b*, 66*c* of increasing size placed there over. The dilators 66*b*, 66*c* are delivered over the obturator 66*a* and k-wire 64 to essentially stretch the skin around the incision 62 and to expand the pathway to the anchor site.

Figure 8:
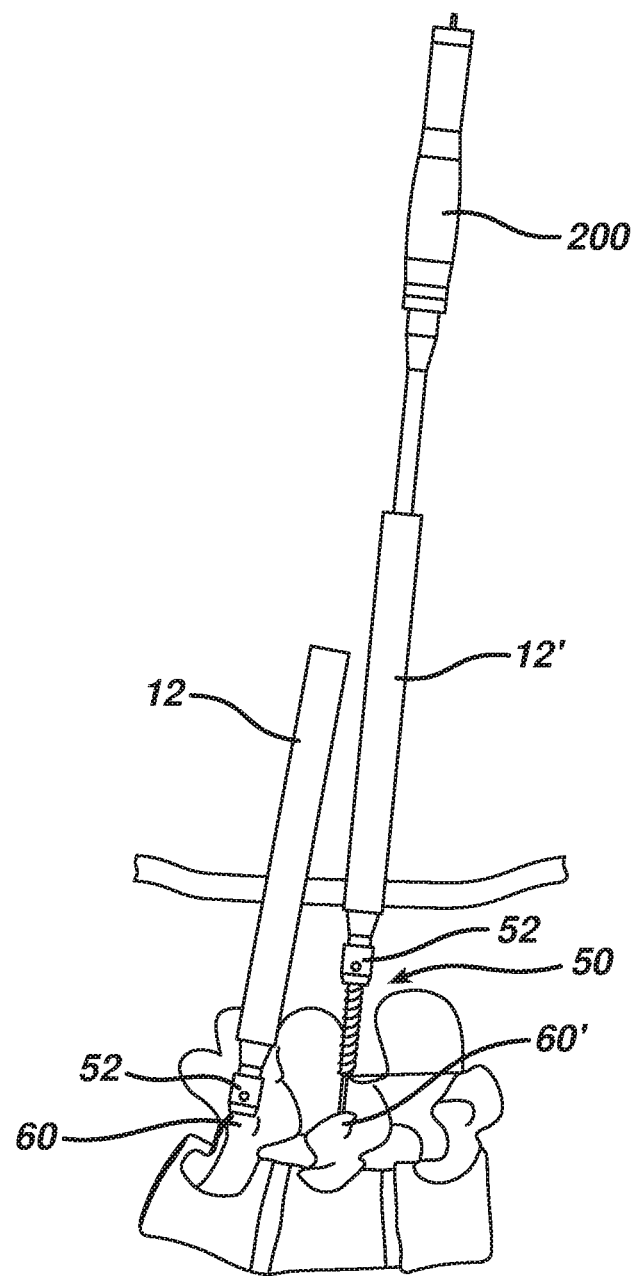
FIG. 8 is perspective view of a first spinal anchor implanted in a vertebra and having a percutaneous access device coupled thereto and extending through a percutaneous incision formed in the patient's tissue surface, and a second spinal anchor being implanted into an adjacent vertebra and having a percutaneous access device coupled thereto with a driver tool extending therethrough.

Once the incision 62 is dilated to the proper size, an anchor can be delivered to each anchor site, as shown in FIG. 8. This procedure typically involves preparation of the vertebra 60 using one or more bone preparation instruments, such as drills, taps, awls, burrs, probes, etc. While not always necessary, one or more cannulae can be used to provide a pathway from the incision 62 to the anchor site for insertion of the bone preparation instruments and/or the anchor. In an exemplary embodiment, a relatively small cannula is used to introduce bone preparation instruments into the surgical site. The incision 62 can then be further dilated, and the small cannula can be replaced with a larger cannula that is adapted to receive or mate to the anchor.

Once the vertebra 60 is prepared, a spinal anchor can be implanted at each implant site. An access device 12, 12' can be mated to each anchor 50, 50' after insertion of the anchor 50, 50' into bone 60, 60', but more preferably each percutaneous access device 12, 12' is attached to the anchor 50, 50' prior to insertion of the anchor 50, 50' into bone 60, 60' to provide a passageway for a driver tool for driving the anchor 50 into bone 60, 60'. FIG. 8 illustrates anchor 50 implanted in a first vertebra 60 and having access device 12 attached thereto. While not shown, the anchor 50 is preferably cannulated to allow the k-wire 64 to extend through the anchor 50 and the access device 12 to guide the devices 50, 12 toward the implant site. FIG. 8 further illustrates a second anchor 50' having an access device 12' mated thereto. As shown, the screw 50' is about to be implanted in a second vertebra 60' that is adjacent to the first vertebra 60. Once the screw 50' is positioned adjacent to the vertebra 60', a driver tool 200 can be positioned through the access device 12' and coupled to the receiver head 52' of the screw 50' to drive the screw 50' into the vertebra 60'.

In another embodiment, a sleeve can be placed over each access device 12, 12', either prior to or after the devices 12, 12', 50, 50' are implanted, to prevent the devices 12, 12' from becoming disengaged from the anchors 50, 50' to which they are attached. The sleeve 100, which is partially illustrated in FIG. 3B, is preferably in the form of a cannula that has substantially the same configuration as each access device 12, 12'. The use of a sleeve is particularly desirable where the access devices 12, 12' utilize pin members that engage corresponding detents formed on an outer surface of each screw head 52, 52', as the sleeve will prevent the pin members from becoming disengaged from the detents. The sleeve can also optionally serve as an access device, allowing access devices 12, 12' to be detached and removed from the anchors 50, 50'.

Figure 9:
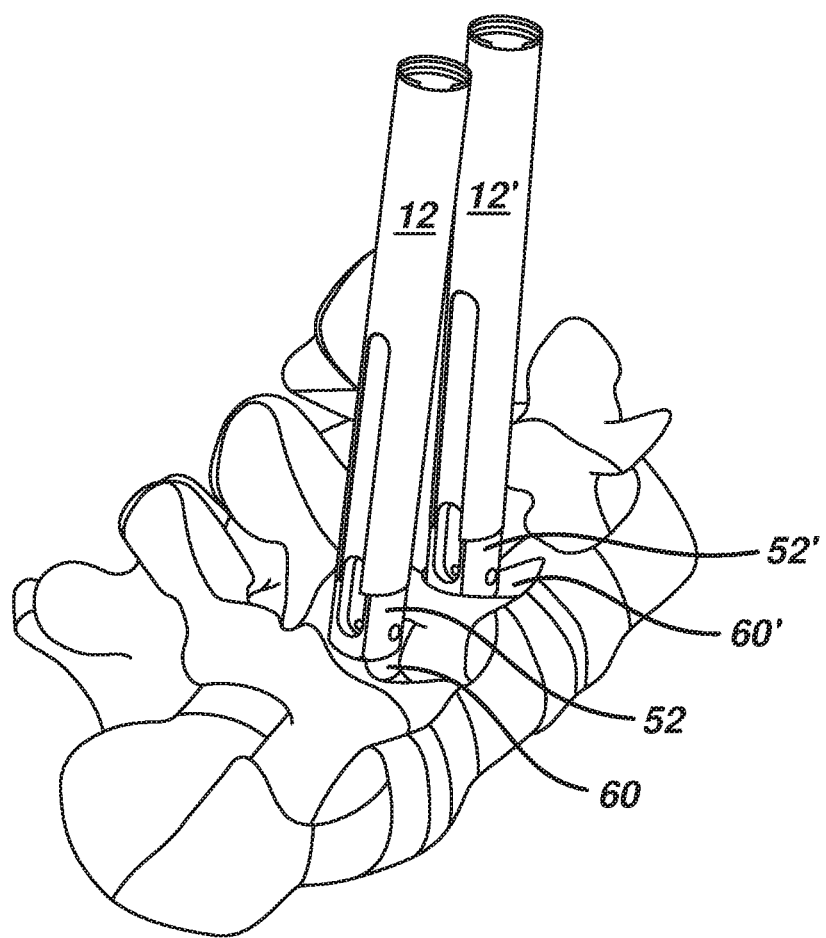
FIG. 9 is a perspective view of two percutaneous access devices attached to spinal anchors that are disposed within adjacent vertebrae in a patient's spinal column.

After the anchors 50, 50' are implanted, a spinal fixation element 70 is delivered to the anchor site. This can be achieved by introducing the spinal fixation element 70 through one of the percutaneous access devices 12, 12' that is attached to the anchor 50, 50', or through some other percutaneous access device that provides a pathway to the anchor(s) 50, 50'. As shown in FIG. 9, a spinal fixation element, e.g., a spinal rod 70, is introduced into device 12 in a first, lengthwise orientation, such that the spinal fixation element 70 is substantially parallel to the longitudinal axis L of the access device 12. Where the fixation element has a curved orientation or it has some other configuration, it is understood that the fixation element is in the "substantially parallel" orientation when it is positioned lengthwise through the percutaneous access device.

Figure 10:
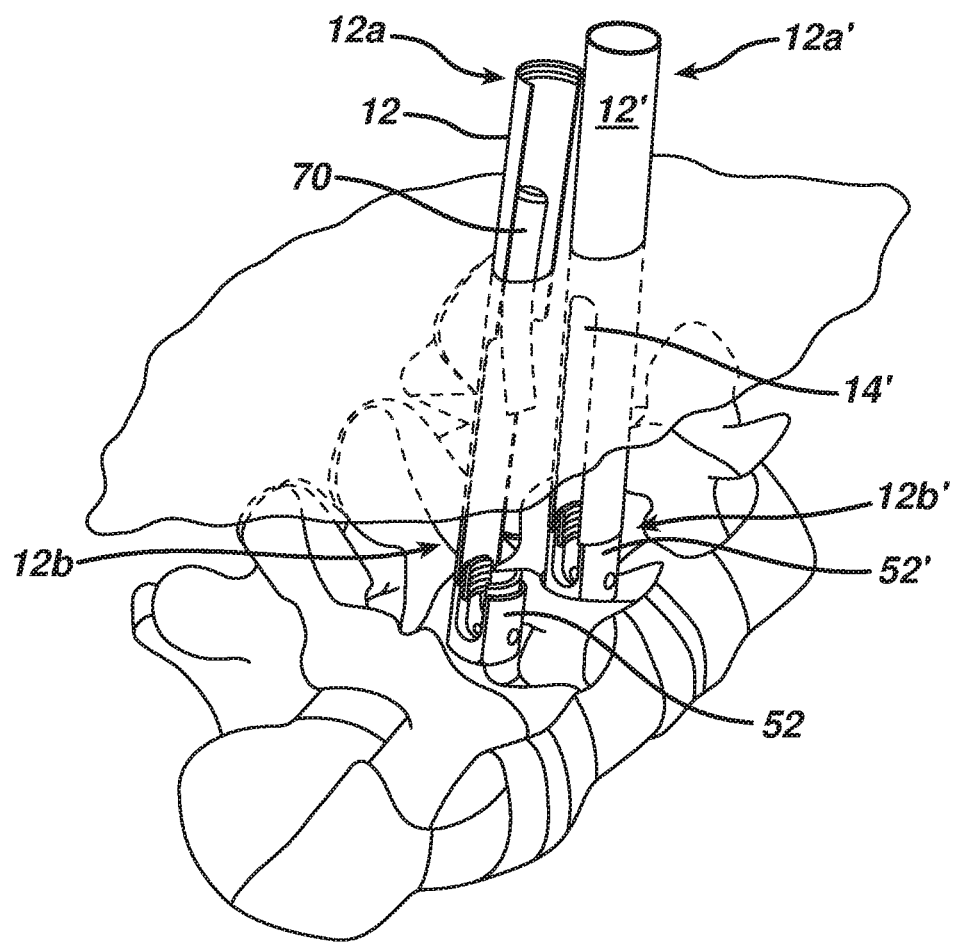
FIG. 10 illustrates a method for introducing a spinal fixation element through a partially cut-away view of one of the percutaneous access devices shown in FIG. 9.
Figure 11:
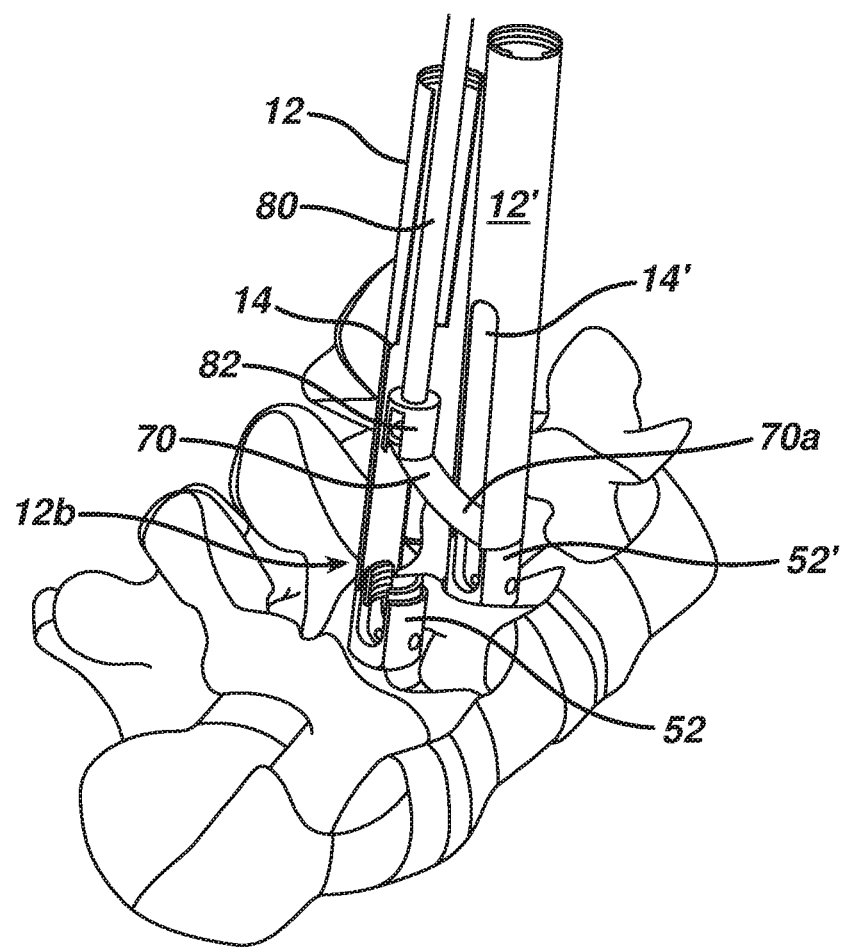
FIG. 11 is a perspective view of the spinal fixation element shown in FIG. 10 being advanced in toward the spinal anchors using a pusher device.

The spinal fixation element 70 is then moved distally toward the distal end 12b of the percutaneous access device 12, as shown in FIGS. 10 and 11. Movement of the spinal fixation element 70 can be achieved using a manipulator device 80. The manipulator device 80 can have a variety of configurations, but it should be effective to allow controlled movement of the fixation element 70. A person skilled in the art will appreciate that a variety of other techniques can be used to guide the spinal fixation element 70 through the percutaneous access device 12 and to position the spinal fixation element 70 in relation to one or more anchors 50, 50'. Moreover, the spinal fixation element 70 can have a variety of configurations to facilitate insertion through a percutaneous access device. By way of non-limiting example, a patent application entitled "Flexible Spinal Fixation Elements," and filed concurrently herewith, discloses a spinal fixation element that can be flexed as it is passed through a percutaneous access device, thereby allowing the spinal fixation element to transition from the first orientation to the second orientation. The application also discloses techniques for delivering the spinal fixation element along a guide wire or cable, thus eliminating the need for a manipulator device. Other spinal fixation elements suitable for use with the present invention, in addition to mechanical and flexible fixation elements, include, for example, inflatable fixation elements such as those disclosed in U.S. Patent Publication No. 2002/0068975, entitled "Formable Orthopedic Fixation System with Cross Linking" by Teitelbaum et al., U.S. Patent Publication No. 2002/0082600, entitled "Formable Orthopedic Fixation System" by Shaolian et al., and U.S. Patent Publication No. 2002/0198526, entitled "Formed In Place Fixation System With Thermal Acceleration" by Shaolian et al., each of which are hereby incorporated by reference in their entirety.

Figure 12:
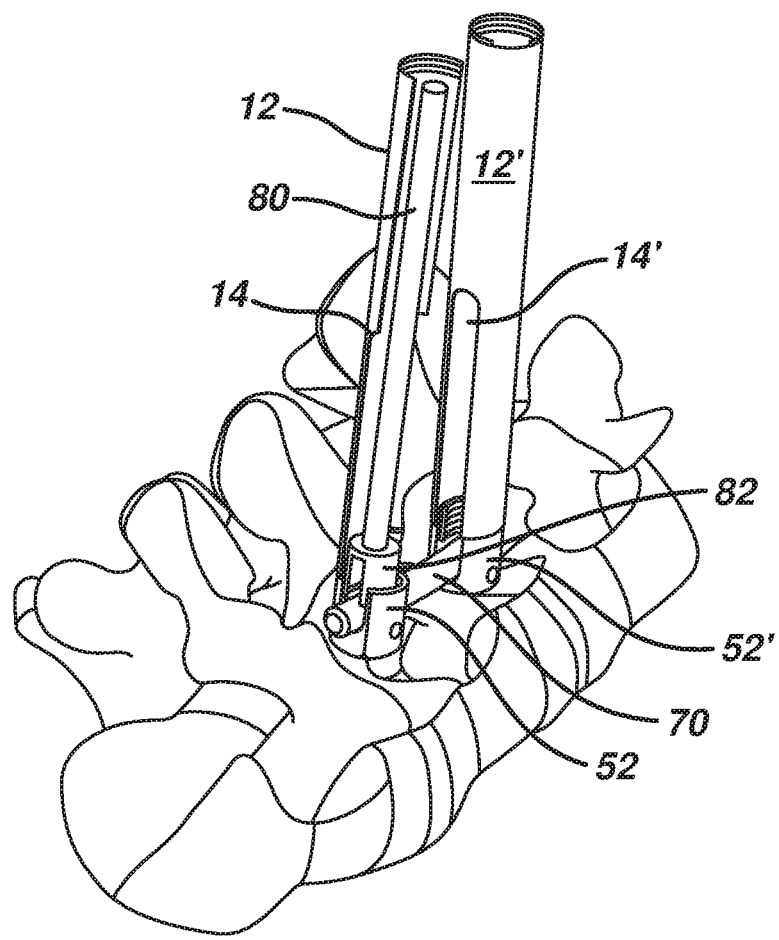
FIG. 12 is a perspective view of the spinal fixation element shown in FIG. 11 after it is fully positioned within receiver heads of the adjacent spinal anchors.

Referring now to FIGS. 11 and 12, as the spinal fixation element 70 approaches the distal end 12b of the access device 12, the spinal fixation element 70 can be manipulated to cause the spinal fixation element 70 to assume a second orientation that is different from the first orientation, and more preferably that is substantially parallel to the patient's spinal column and/or transverse to the first orientation. It is understood that the angle of the fixation element 70 in the second orientation will vary depending on the type of fixation device being implanted, as well as the orientation of the access device 12, which can vary throughout the surgical procedure since the access device 12 can be positioned at several angles with respect to the patient's spinal column.

During transition of the spinal fixation element 70 from the first orientation to the second orientation, a leading end of the spinal fixation element 70 should be subcutaneously positioned. Where the access device 12 includes slots or openings (only one opening 14 is shown), the opening(s) 14 can be used to facilitate movement of the spinal fixation element 70 into the second orientation as they will allow the spinal fixation element 70 to extend therethrough during rotation. This may not be necessary, however, depending on the length of the openings 14, the length of the spinal fixation element 70, and/or the configuration of the spinal fixation element 70. As shown in FIGS. 11 and 12, only the leading end 70a of the spinal fixation element 70 exits the percutaneous access device 12 through one of the openings 14.

Referring to FIG. 12, manipulation of the spinal fixation element 70 is continued until the spinal fixation element 70 is positioned in relation to one or more spinal anchors. Depending on the type of spinal anchor used, the fixation element can be positioned to be directly or indirectly mated to the spinal anchor. As shown in FIG. 12, the fixation element 70 is fully seated in the receiver heads 52, 52' of the adjacent spinal anchors 50, 50'. The manipulator device 80, if used, can then be removed from the access device 12.

In another embodiment, the percutaneous access device 112 shown in FIGS. 3A and 3B can be used to facilitate introduction of a spinal fixation element into a surgical anchor site. As previously stated, access device 112 includes a guide member 20 formed therein to direct the spinal fixation element 70 from the first orientation to the second orientation. This is illustrated in FIGS. 13-16. As shown, as the spinal fixation element 70 is moved distally to come into contact with the guide member 120, the guide member 120 causes the spinal fixation element 70 to rotate and extend toward the opening 114 in the percutaneous access device 112. As a result, the spinal fixation element 70 is directed into the second orientation, whereby it can be positioned in or adjacent to the receiver heads 52, 52' of the adjacent spinal implants 50, 50'.

Referring back to FIG. 12, once the spinal fixation element 70 is fully seated in the receiver heads 52, 52' of the adjacent spinal anchors 50, 50', the pusher shaft 80, if used, can then be removed or detached from the spinal fixation element 70, and a closure mechanism can be applied to one or both receiver heads 52, 52' to retain the spinal fixation element 70 therein. In an exemplary embodiment, however, a compression tool 100 is used to compress the access devices 12, 12' toward one another prior to applying a closure mechanism to each anchor 50, 50'. The closure mechanism(s) can, however, be partially applied before compression.

Figure 17:
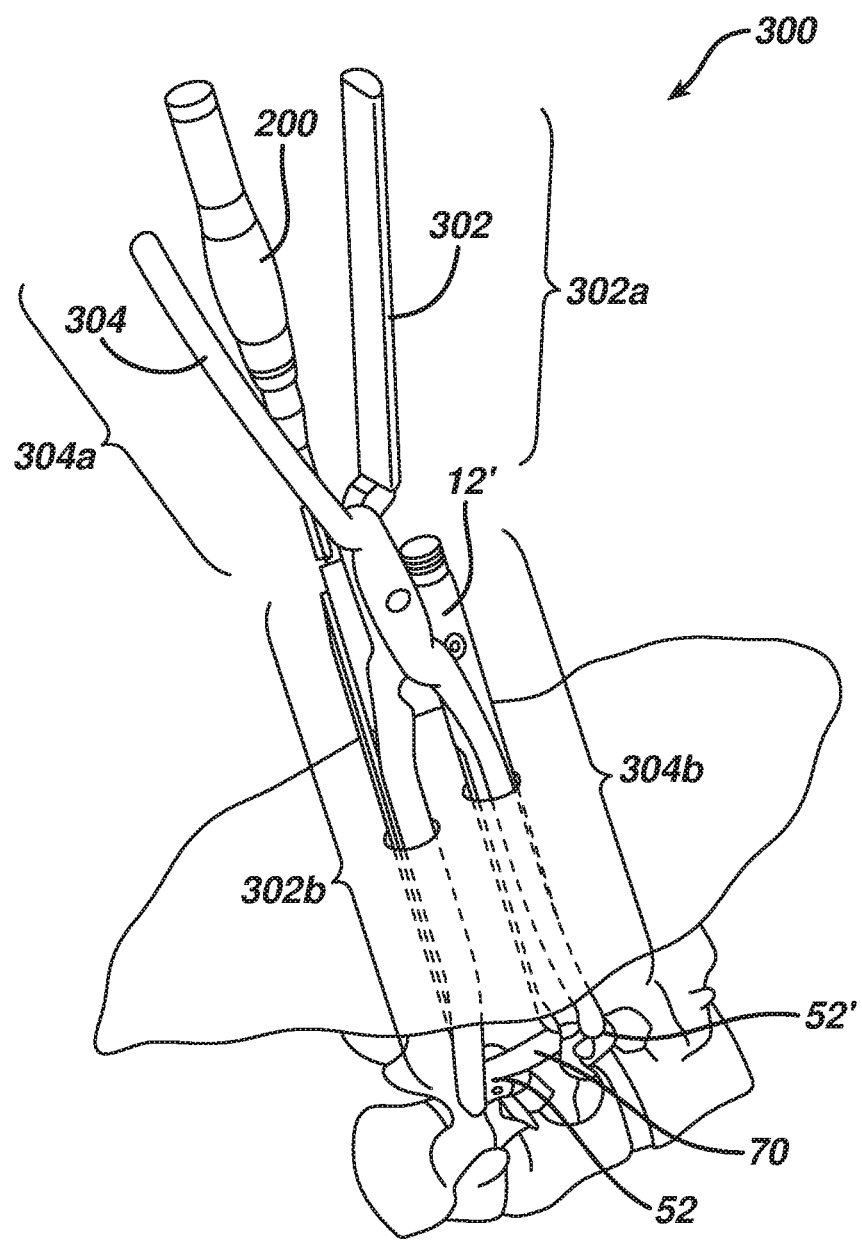
FIG. 17 is a perspective view of a compression tool positioned around the percutaneous access devices shown in FIG. 12 and compressing the devices toward one another, and a closure mechanism being applied through one of the percutaneous access devices to lock the spinal fixation element in relation to the spinal anchor.
Figure 18:
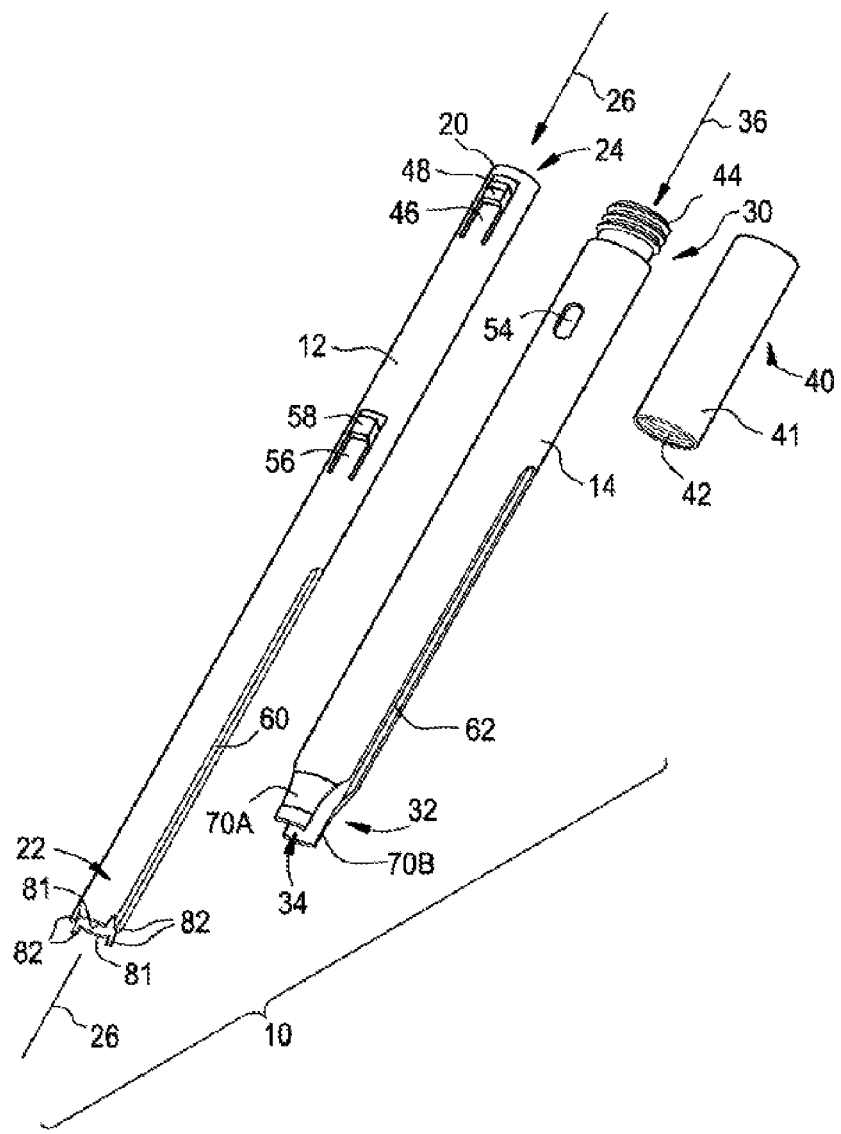
FIG. 18 is a perspective view of the components of a percutaneous access device.
Figure 19:
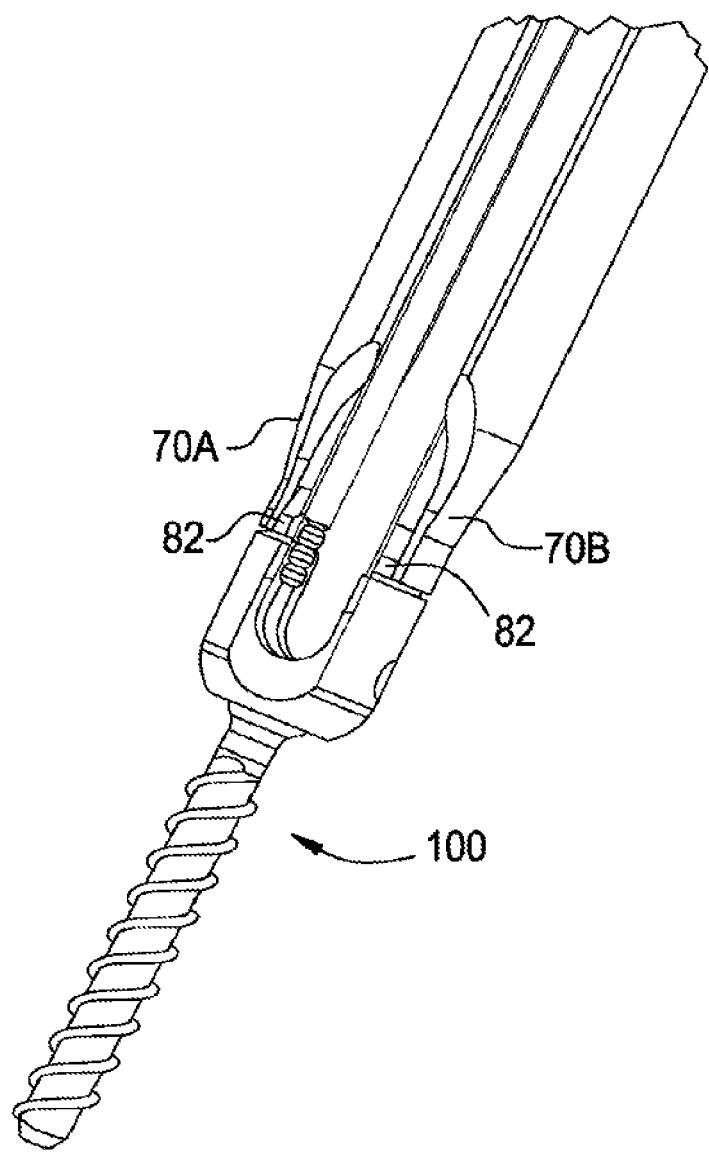
FIG. 19 is a perspective view of the distal end of the percutaneous access device of FIG. 18 coupled to an exemplary embodiment of a bone anchor assembly.
Figure 20:
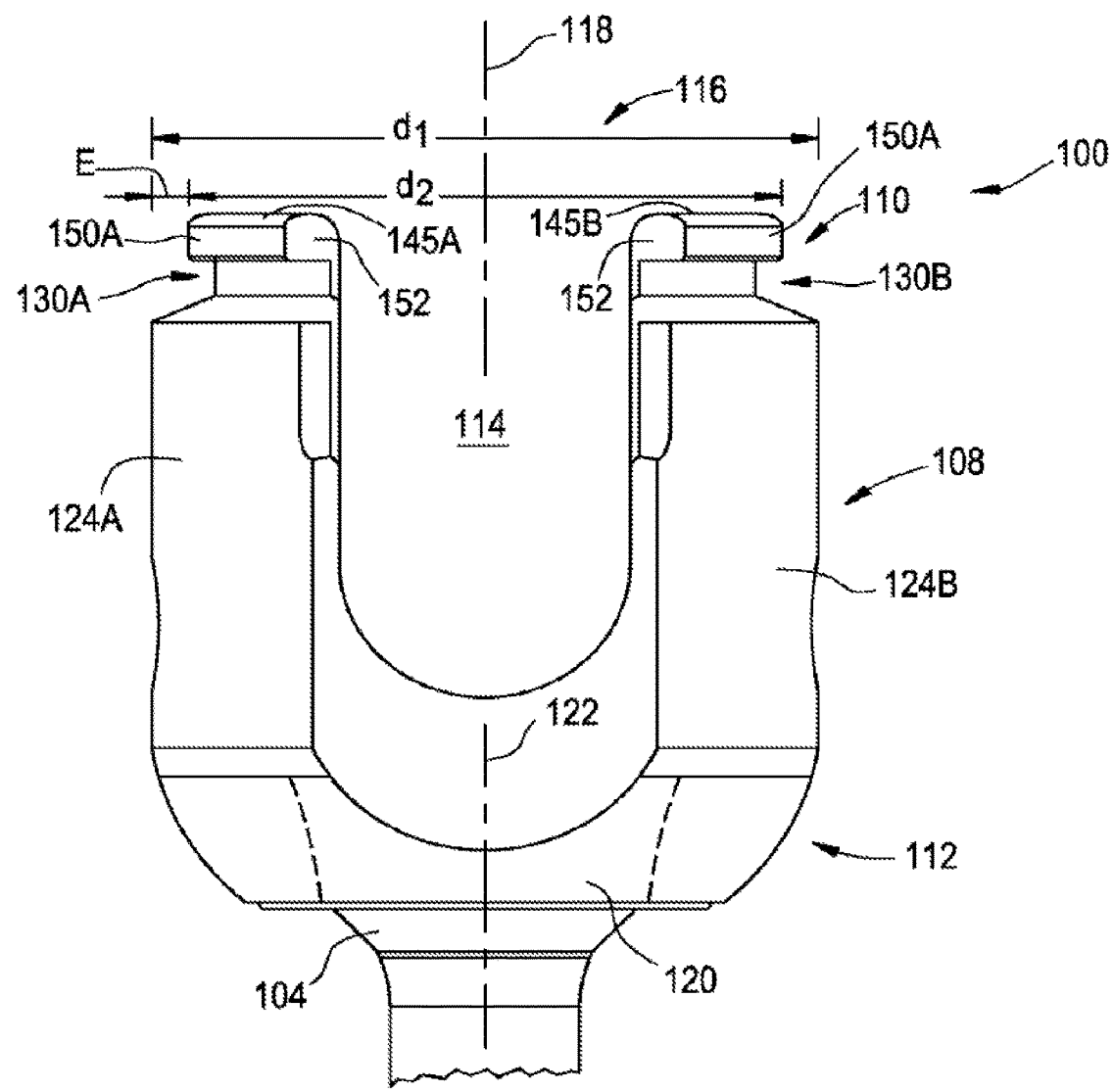
FIG. 20 is a side elevational view of the receiving member of the bone anchor assembly of FIG. 19.
Figure 21:
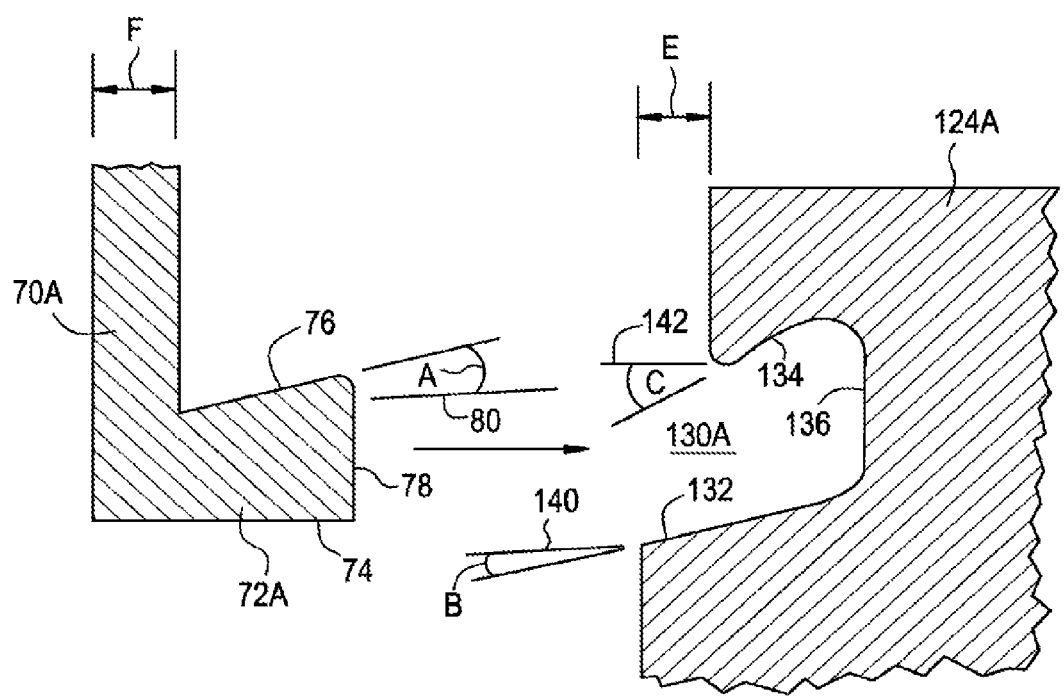
FIG. 21 is a side elevational view in cross-section of the distal end of the outer tube of the percutaneous access device of FIG. 18 and the receiving member of the bone anchor assembly of FIG. 19.

An exemplary compression tool 300 is shown in FIG. 17, and in general it includes opposed arms 302, 304 that are pivotally coupled to one another at a substantial mid-point thereof such that each arm 302, 304 includes a distal portion 302b, 304b that is adapted to be disposed around a percutaneous access device 12, 12', and a proximal, handle portion 302a, 304a. The device 300 can also include a fulcrum (not shown) that is disposed between the arms 302, 304 to facilitate controlled movement of the arms 302, 304 with respect to one another. In use, the distal portion 302b, 304b of each arm 302, 304 is placed around an access device 12, 12', preferably around the distal end 12b, 12b' of each device 12, 12' and/or around the head 52, 52' of each anchor 50, 50'. The proximal, handle portions 302a, 304a are then brought toward one another to move the access devices 12, 12' toward one another, preferably while maintaining relative spacing therebetween, as shown in FIG. 17.

Figure 13:
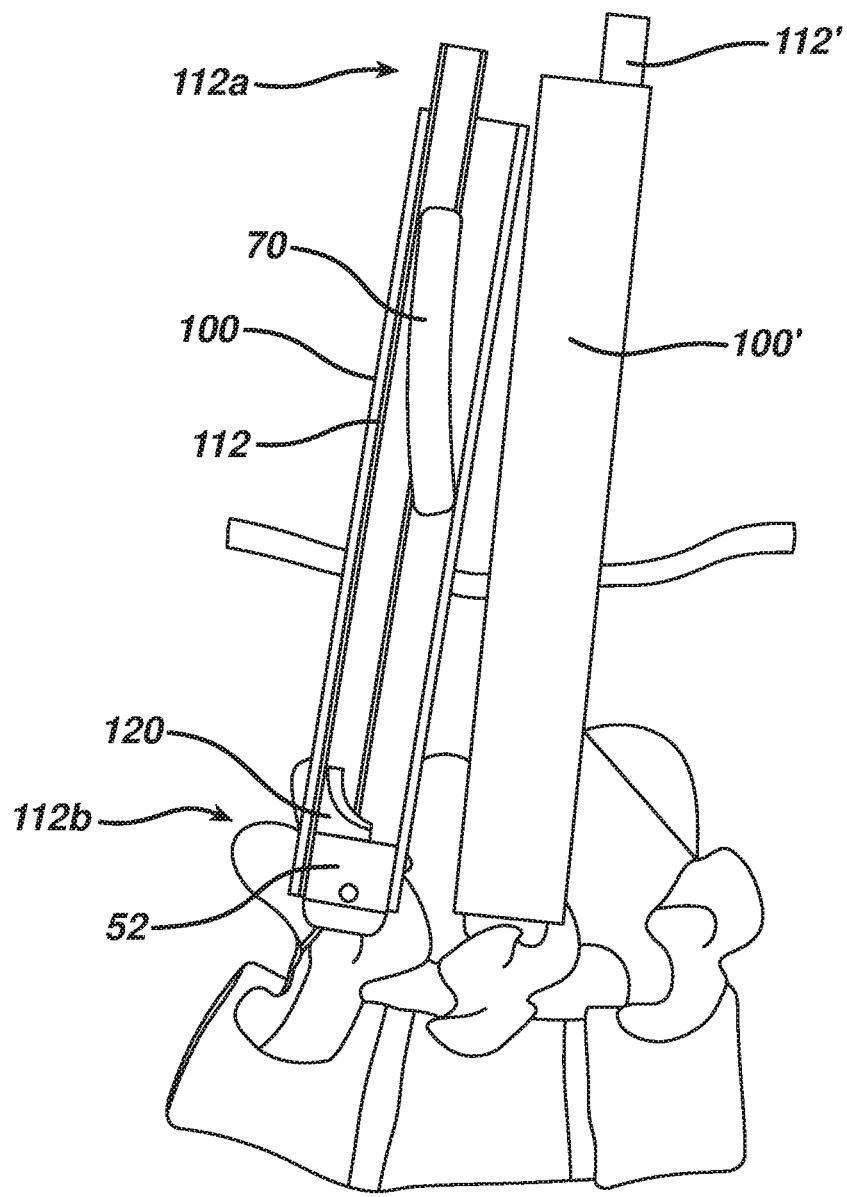
FIG. 13 illustrates a method for introducing a spinal fixation element through a partially cut-away view of the percutaneous access device shown in FIGS. 3A and 3B.
Figure 14:
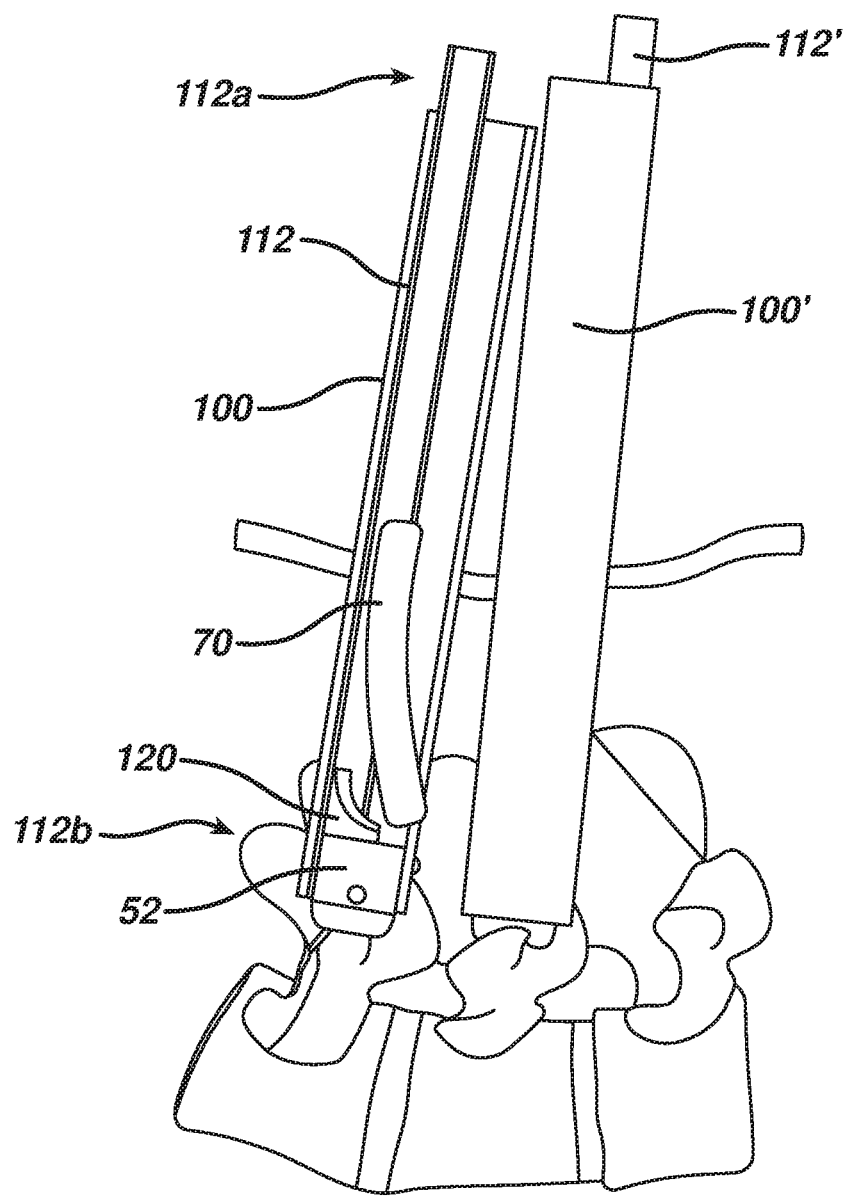
FIG. 14 is a perspective view of the spinal fixation element shown in FIG. 13 being advanced toward the spinal anchors using a pusher device.
Figure 15:
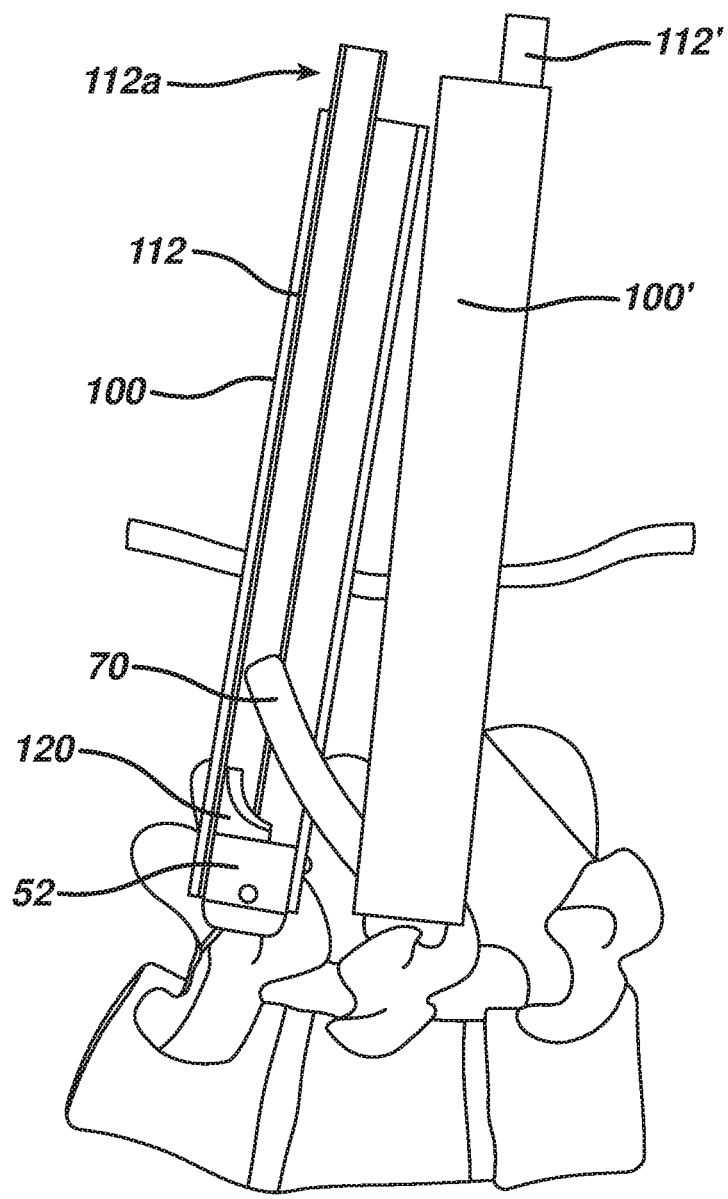
FIG. 15 is a perspective view of the spinal fixation element shown in FIG. 14 advanced further toward the receiver heads of the adjacent spinal anchors.
Figure 16:
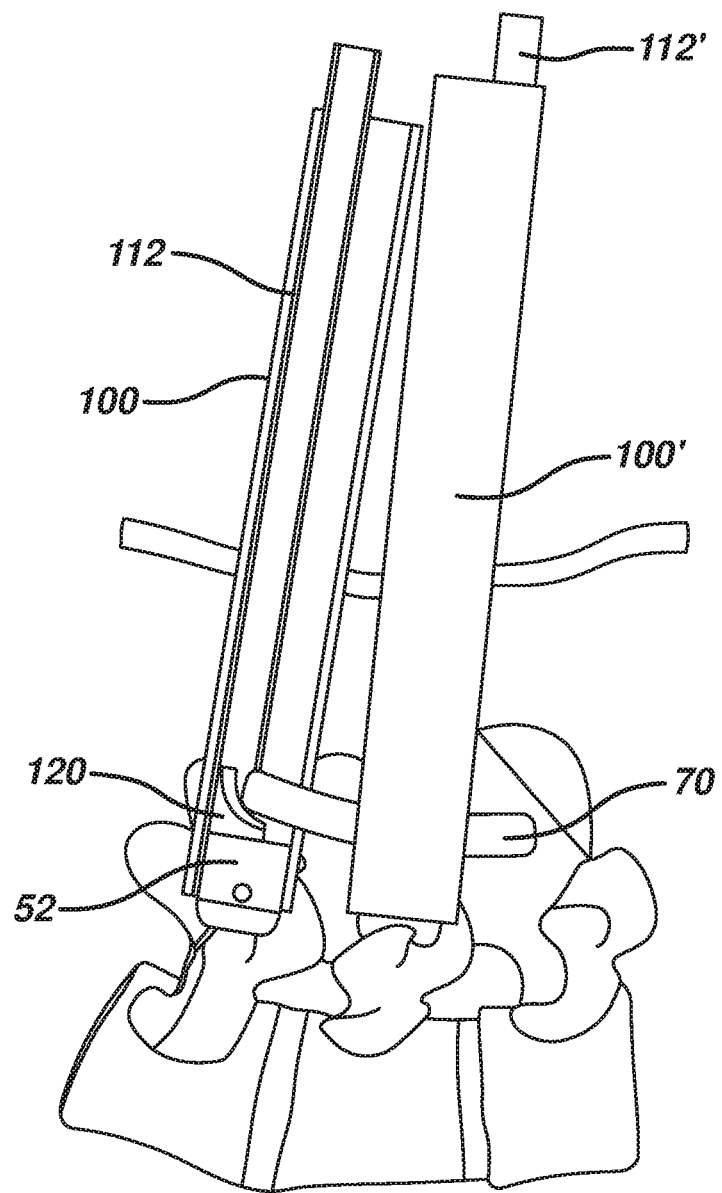
FIG. 16 is a perspective view of the spinal fixation element shown in FIG. 15 about to be disposed within the receiver heads of the adjacent spinal anchors.

Once properly positioned, a closure mechanism can be applied, preferably via the access devices 12, 12', to each anchor head 50, 50' to retain the spinal fixation element 70 within the receiver heads 52, 52'. A variety of closure mechanisms and tools for delivering closure mechanisms are known in the art and they can be used with the present invention. By way of non-limiting example, FIG. 13 illustrates driver tool 200 disposed through access device 12 for applying a closure mechanism, such as a set screw, to the receiver head 52 of the spinal anchor 50 to lock the spinal fixation element 70 with respect to the spinal anchor 50. This step can be repeated for the adjacent spinal anchor(s).

A person skilled in the art will appreciate that the spinal fixation element 70 does not need to be directly attached to each anchor 50, 50', and that it can be indirectly attached to the anchors 50, 50' using, for example, a band clamp, or slotted or offset connectors.

Once the fixation element 70 is secured in relation to the implants 50, 50', the access devices 12, 12' can be removed from the implants 50, 50', leaving only minimally invasive percutaneous incisions in the patient where each access device 12, 12' was introduced. This is particularly advantageous in that it reduces the amount of trauma caused to the patient, and it minimizes the damage to muscle surrounding the surgical site.

As previously stated, a person skilled in the art will appreciate that the method can be performed in any sequence using any of the steps. Moreover, the access devices of the present invention can be used to deliver multiple spinal fixation elements simultaneously or sequentially, and/or to perform a variety of other surgical procedures not illustrated or described herein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

In embodiments in which multiple slots are employed, the slots 60, 62 need not be similarly sized (width and/or length). For example, the one or more slots 60 may be sized differently than the one or more slots 62, the one or more of the slots 60 on the inner tube may be sized differently than other slots 60, and/or one or more of the slots 62 on the outer tube may be sized differently than other slots 62. Although the exemplary embodiment includes two opposing slots on the inner tube 12 and the outer tube 14, respectively, one skilled in the art will appreciate that any number of slots may be provided, e.g., no slots, one, two, three, etc. slots, may be provided depending on the method, instruments, and/or fixation element employed.

The distal end 32 of the outer tube 14 includes a pair of opposed longitudinally extending tabs 70A and 70B that may releasably engage a bone anchor. In the exemplary embodiment, the tabs 70A and 70B are defined by the sidewalls of the outer tube 14 and are separated by slots 62A and 62B. In certain exemplary embodiments, the tabs 70A and 70B may be flexible and resilient in the radial direction to facilitate connection to a bone anchor. For example, the tabs 70A and 70B may be flexed apart in the radial direction from a first, relaxed position to facilitate advancement of the tabs longitudinally over a portion of the bone anchor. Once positioned about a portion of the bone anchor, the tabs 70A and 70B may provide a radially compressive force on the bone anchor as the tabs 70A and 70B attempt to return to the first, relaxed position. In other exemplary embodiments, including the exemplary percutaneous access device 10, the tabs 70A and 70B need not be flexible and resilient.

The receiving member 108 of the exemplary bone anchor assembly 100 is configured to be releasably connected to an instrument such as the exemplary percutaneous access device 10 described above. For example, the receiving member 108 may include at least one groove 130 that is configured to receive a portion of an instrument to releasably connect the instrument to the bone anchor assembly. The size, shape, position, and number of grooves can be varied depending on, for example, the instrument employed and the type of connection desired. In certain embodiments, for example, at least one arcuate groove 130 may be provided on an exterior surface of the proximal end 110 of the receiving member 108. In other exemplary embodiments, at least one arcuate groove may be provided on an interior surface of the proximal end 110 of the receiving member 108. In the illustrated exemplary embodiment, each leg 124A and 124B may be provided with an arcuate groove 130A, 130B, respectively, at the free, proximal end of the leg 124A, 124B. The grooves 130A, 130B may extend about a portion or all of the circumference of the proximal end of each leg 124A, 124B. Each groove 130A, 130B may have size and shape that is complementary in size and shape to a projection provided on the instrument. For example, in the illustrated exemplary embodiment, the each groove 130A, 130B may be arcuate and may have a cross-section complementary to the cross-section of a projection 72A,72B provided on the tabs 70A,70B of the outer sleeve 14. In particular, groove 130 may have a distal surface 132, a proximal surface 134 and an interconnecting surface 136 that spans between the distal surface 132 and the proximal surface 134, as illustrated in FIG. 8. The distal surface 132 and/or the proximal surface 134 may be oriented to facilitate insertion of a projection into the grove 130 and/or to inhibit undesirable separation of the projection from the groove 130. In the illustrated exemplary embodiment, for example, the distal surface 132 may be generally oriented at an angle B to an orthogonal line 140, which is oriented perpendicular to the longitudinal axis of the receiving member 108, to facilitate insertion of the projection into the groove. In the exemplary embodiment, the angle B may be approximately 0° to approximately 45° and preferably approximately 30° to 40°. In the illustrated exemplary embodiment, the proximal surface 134 may be oriented at an angle other than perpendicular to longitudinal axis of the receiving member 108 to inhibit separation of the projection from the groove 130, particularly in radial direction. For example, the proximal surface 134 may be oriented at an angle C to an orthogonal line 142, which is perpendicular to the longitudinal axis of the receiving member 108. In the exemplary embodiment, the angle C may be approximately 5° to approximately 30° and is preferably approximately 20°. The distal surface 132 and the proximal surface 76 may be oriented at the same angle or, as in the exemplary embodiment, may be oriented at different angles. The grooves 130A and 130B, as well as any additional grooves, may have similar cross-sectional geometries, as in the case of the illustrated exemplary embodiment, or may have distinct geometries.

The invention claimed is:

1. A method for implanting a rod implant along a spine of a patient back, the method comprising:
   a) minimally invasively passing the rod implant distally through a first minimally invasive incision in the patient back by causing a first end of the rod implant to distally displace along a first central longitudinal channel of a first elongated guide tool minimally invasively extending through the first minimally invasive incision from a first connection of a distal region of the first elongated guide tool to a head of a first bone anchor at a proximal region of the first bone anchor, the first bone anchor implanted in a first vertebra of the spine, and the head comprising a first rod-receiving channel;
   b) after the first end has minimally invasively passed through the first minimally invasive incision as recited in step a), exiting the first end from the first central longitudinal channel via a first longitudinally extending side slot of the first elongated guide tool and displacing the first end towards a second elongated guide tool along a trajectory diagonal to a longitudinal axis of the first elongated guide tool, the second elongated guide tool minimally invasively extending through a second minimally invasive incision from a second connection of a distal region of the second elongated guide tool to a head of a second bone anchor at a proximal region of the second bone anchor, the second bone anchor implanted in a second vertebra of the spine, and the head of the second bone anchor comprising a second rod-receiving channel;
   c) entering the first end into a second central longitudinal channel of the second elongated guide tool via a second longitudinally extending side slot of the second elongated guide tool; and
   d) causing the rod implant near the first end to enter the second rod-receiving channel and the implant rod near a second end of the rod implant opposite the first end to enter the first rod-receiving channel.

2. The method of claim 1, wherein, in achieving the steps recited in step d), the first end projects through a third longitudinally extending side slot of the second elongated guide tool opposite the second side slot.

3. The method of claim 2, wherein, further in achieving the steps recited in step d), the second end projects through a fourth longitudinally extending side slot of the first elongated guide tool opposite the first side slot.

4. The method of claim 3, wherein the first and fourth longitudinally extending side slots comprise different lengths.

5. The method of claim 4, wherein the first longitudinally extending side slot is longer than the fourth longitudinally extending side slot.

6. The method of claim 2, wherein the second and third longitudinally extending side slots comprise different lengths.

7. The method of claim 6, wherein the second longitudinally extending side slot is longer than the third longitudinally extending side slot.

8. The method of claim 1, wherein the first connection is a result of spaced-apart opposed legs of the distal region of the first elongated guide tool splaying apart as the head of the first bone anchor is forced proximally between the spaced-apart opposed legs, a feature of at least one of the legs snapping into engagement with a groove defined in a radially outward cylindrical surface of the head of the first bone anchor.

9. The method of claim 8, further comprising application of a force directed to proximally displace the spaced-apart opposed legs relative to the head of the first bone anchor once the feature is received in the groove.

10. The method of claim 9, wherein the groove comprises a planar boundary perpendicular to a longitudinal center axis of the head of the first bone anchor and perpendicularly intersecting the radially outward cylindrical surface of the head of the first bone anchor, the planar boundary making complementary planar surface contact with the feature when the feature is received in the groove.

11. The method of claim 8, further comprising application of a force directed to proximally displace the spaced-apart opposed legs relative to the head of the first bone anchor, thereby setting the feature in the groove in a manner that inhibits splaying apart of the spaced-apart opposed legs.

12. The method of claim 11, wherein the groove comprises a recessed overhanging configuration at a proximal boundary of the groove, and the feature comprises a proximally pointing free extent that is received by the recessed overhanging configuration.

13. The method of claim 1, further comprising delivering a threaded closure top into the first rod-receiving channel via a route extending along the first central longitudinal channel, and threading the threaded closure top into the first rod-receiving channel to secure the rod implant within the first rod-receiving channel.

14. The method of claim 1, further comprising rotating the first elongated guide tool relative to the head of the first bone anchor to disconnect the first elongated guide tool from the head of the first bone anchor.

15. The method of claim 1, wherein the first and fourth side slots are aligned with the first rod-receiving channel when the rod implant enters the first rod-receiving channel.

16. The method of claim 1, wherein a width of the first side slot along a length of the first side slot is narrower than another width of the first side slot near a distal end of the first side slot.

17. The method of claim 1, wherein, in achieving the steps recited in step d), an elongated member distally displaces along the first central longitudinal channel of the first elongated guide tool to distally drive the rod implant from the first central longitudinal channel into the second rod-receiving channel.

18. The method of claim 1, wherein step b) further comprises causing the first end to pass through a fifth longitudinally extending side slot of a third elongated guide tool and a sixth longitudinally extending side slot of the third elongated guide tool as the first end is displaced towards the second elongated guide tool from the first longitudinally extending side slot of the first elongated guide tool, the fifth and sixth longitudinally extending side slots opposite each other and the third elongated guide tool minimally invasively extending through a third minimally invasive incision from a third connection of a distal region of the third elongated guide tool to a head of a third bone anchor at a proximal region of the third bone anchor, the third bone anchor implanted in a third vertebra of the spine, and the head of the third bone anchor comprising a third rod-receiving channel.

19. The method of claim 18, wherein step d) further comprises causing the rod implant intermediate the first and second ends to enter the third rod-receiving channel.

20. The method of claim 18, wherein the fifth and sixth longitudinally extending side slots comprise different lengths.

21. The method of claim 1, wherein at least one of the first or second bone anchor comprises a bone screw.

22. The method of claim 21, wherein the bone screw is at least one of polyaxial or cannulated.

* * * * *